US000002022H

(19) United States

(12) Statutory Invention Registration (10) Reg. No.: US H2022 H

Heidler et al. (43) Published: May 7, 2002

(54) INOSITOLPHOSPHORYL CERAMIDE (IPC) SYNTHASE GENES FROM FUNGI

(75) Inventors: Steven Alan Heidler, Fishers; Jeffrey Alan Radding, Carmel, both of IN (US)

(73) Assignee: Eli Lilly and Company, Indianapolis, IN (US)

(21) Appl. No.: 09/041,075

(22) Filed: Mar. 10, 1998

Related U.S. Application Data

(60) Provisional application No. 60/043,591, filed on Apr. 15, 1997, provisional application No. 60/044,095, filed on Apr. 22, 1997, provisional application No. 60/046,348, filed on May 13, 1997, provisional application No. 60/053,320, filed on Jul. 21, 1997, provisional application No. 60/062,971, filed on Oct. 17, 1997, and provisional application No. 60/076,436, filed on Mar. 2, 1998.

(51) Int. Cl.[7] ..... C12N 9/12

(52) U.S. Cl. ..... 435/194; 435/254.22

(58) Field of Search ..... 435/193, 194, 435/254.22

(56) References Cited

U.S. PATENT DOCUMENTS 6,022,949 A * 2/2000 Okado et al. ..... 530/350

FOREIGN PATENT DOCUMENTS

EP 0 768 380 A2 1/1996

OTHER PUBLICATIONS

Hackett et al. FEBS Letters, vol. 74, p. 259–263, Mar. 1977.*

Takashi Hashida–Okado, et al. "AUR1, a novel gene conferring aureobasidin resistance on *Saccharomyces cerevisiae*: a study of defective morphologies in Aur1 p–depleted cells." *Mol Gen Genet* 251:236–244 (1996).

Takashi Hashida–Okado, et al. "Isolation and characterization of the aureobasidin A–resistant gene, aur1$^R$, on *Schizosaccharomyces pombe:* roles of Aur1 p$^+$ in cell morphogenesis." *Curr Genet* 33:38–45 (1998).

Steven A. Heidler and Jeffrey A. Radding. "The AUR1 Gene in *Saccharomyces cerevisiae* Encodes Dominant Resistance to the Antifungal Agent Aureobasidin A (LY295337)." *Antimicrobial Agents and Chemotherapy* 39(12):2765–2769 (Dec. 1995).

M. Marek Nagiec, et al. "Sphingolipid Synthesis as a Target for Antifungal Drugs." *The Journal of Biological Chemistry* 272(15):9809–9817 (Apr. 11, 1997).

* cited by examiner

*Primary Examiner*—Michael J. Carone
*Assistant Examiner*—Aileen J. Baker
(74) *Attorney, Agent, or Firm*—Charles E. Cohen; Thomas D. Webster

(57) ABSTRACT

The invention provides isolated nucleic acid compounds encoding IPC synthase or subunit thereof from fungal cells. Also provided are vectors and transformed heterologous host cells for expressing IPC synthase and a method for identifying compounds that inhibit a fungal IPC synthase.

2 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

INOSITOLPHOSPHORYL CERAMIDE (IPC) SYNTHASE GENES FROM FUNGI

This application claims benefit to U.S. Provisional application Nos. 60/043,591, filed Apr. 15, 1997, 60/044,095, filed Apr. 22, 1997, 60/046,348, filed May 13, 1997, 60/053,320, filed Jul. 21, 1997, 60/062,971, filed Oct. 17, 1997, 60/076,436, filed Mar. 2, 1998.

BACKGROUND OF THE INVENTION

This invention relates to recombinant DNA technology. In particular the invention pertains to the isolation of novel genes and proteins that encode inositolphosphoryl ceramide synthase (IPC) synthase or subunit thereof from a variety of fungi and the use of said proteins in screens for inhibitors of IPC Synthase.

The incidence of life-threatening fungal infections is increasing at an alarming rate. With the exception of Staphylococci infections, the fungus *C. albicans* represents the fastest growing area of concern in hospital acquired bloodstream infections. About 90% of nosocomial fungal infections are caused by species of Candida with the remaining 10% being attributable to infections by Aspergillus, Cryptococcus, and Pneumocystis. While effective antifungal compounds have been developed for Candida there is growing concern that the rise in the incidence of fungal infections may portend greater resistance and virulence in the future. Moreover, anti-Candida compounds frequently do not possess clinically significant activity against other fungal species.

Inositolphosphoryl ceramides are sphingolipids found in a number of fungi including but not limited to *S. cerevisiae, S. pombe, C. albicans, A. fumigatus, A. nidulans* and *H. capsulatum.* A step of sphingolipid biosynthesis unique to fungi and plants is catalyzed by the enzyme IPC synthase. The IPC synthase step, covalently links inositol phosphate and ceramide, and is essential for viability in *S. cerevisiae.* Although some elements of sphingolipid biosynthesis in fungi are shared with mammalian systems, the pathways diverge at the step after formation of ceramide. Thus, the formation of inositolphosphoryl ceramide is unique to fungi and plants, making IPC synthase a good molecular target for antifungal chemotherapy.

While compounds that target IPC synthase bode well for the future of anti-fungal therapy, presently there are no clinically useful compounds that act at this step. Thus, there is a need for new compounds that inhibit IPC synthase.

BRIEF SUMMARY OF THE INVENTION

The present invention relates to fungal IPC synthase and to screens for inhibitors thereof.

In one embodiment the invention relates to fungal genes that encode IPC synthase, or subunit thereof.

In another embodiment, the invention relates to fungal IPC synthase genes identified herein as SEQ ID NO:1, SEQ ID NO:4, SEQ ID NO:7, SEQ ID NO:10, SEQ ID NO:19, and SEQ ID NO:20.

In another embodiment, the invention relates to nucleic acids that are at least 70% homologous, and/or, will hybridize under high stringency conditions to a sequence identified herein as SEQ ID NO:1, SEQ ID NO:4, SEQ ID NO:7, SEQ ID NO:10, SEQ ID NO:19, and SEQ ID NO:20.

In another embodiment the present invention pertains to the proteins produced by IPC synthase genes.

In yet another embodiment, the invention relates to proteins designated herein as SEQ ID NO 2, SEQ ID NO 5, SEQ ID NO 8, SEQ ID NO 11, and SEQ ID NO:21.

In still another embodiment the invention relates to the use of purified fungal IPC synthase or subunit thereof in high throughput screens for inhibitors of fungal IPC synthase, said IPC synthase being designated herein as SEQ ID NO:2, SEQ ID NO:5, SEQ ID NO:8, SEQ ID NO:11, SEQ ID NO:14, SEQ ID NO:17, and SEQ ID NO:21.

In another embodiment the invention relates to the use of recombinant host cells that carry a vector that expresses a fungal IPC synthase in high throughput screens for inhibitors of fungal IPC synthase.

In another embodiment the invention relates to the use of the IPC synthase genes disclosed herein, or fragments thereof, as hybridization probes or PCR primers to identify and isolate homologous genes that are related in sequence and/or function.

DEFINITIONS

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature.

The term "fusion protein" denotes a hybrid protein molecule not found in nature comprising a translational fusion or enzymatic fusion in which two or more different proteins or fragments thereof are covalently linked on a single polypeptide chain.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refers to the capacity of purine and pyrimidine nucleotides to associate through hydrogen bonding in double stranded nucleic acid molecules. The following base pairs are complementary: guanine and cytosine; adenine and thymine; and adenine and uracil.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a nucleic acid compound that hybridizes with another nucleic acid compound, and is useful for blot hybridizations, for example. A probe is at least 15 base pairs in length, its sequence being at least 90% identical with the nucleic acid molecules disclosed herein, or fragments thereof, or the complements thereof. A probe may or may not be labeled with a detectable moiety. As used herein, a probe is useful for hybridization analysis to identify sequences homologous to those disclosed herein.

The term "hybridization" as used herein refers to a process in which a single-stranded nucleic acid molecule joins with a complementary strand through nucleotide base pairing. "Selective hybridization" refers to hybridization under conditions of high stringency. The degree of hybridization depends upon, for example, the degree of complementarity, the stringency of hybridization, and the length of hybridizing strands.

The term "stringency" refers to hybridization conditions. High stringency conditions disfavor non-homologous base-pairing. Low stringency conditions have the opposite effect. Stringency may be altered, for example, by temperature and salt concentration.

"Low stringency" conditions comprise, for example, a temperature of about 37° C. or less, a formamide concentration of less than about 50%, and a moderate to low salt (SSC) concentration; or, alternatively, a temperature of about 50° C. or less, and a moderate to high salt (SSPE) concentration.

"High stringency" conditions comprise a temperature of about 42° C. or less, a formamide concentration of less than about 20%, and a low salt (SSC) concentration; or, alternatively, a temperature of about 65° C., or less, and a low salt (SSPE) concentration.

"SSC" comprises a hybridization and wash solution. 20X SSC contains 3M sodium chloride, 0.3M sodium citrate, pH 7.0.

"SSPE" comprises a hybridization and wash solution. 1X SSPE contains 180 mM NaCl, 9mM $Na_2HPO_{4,0.9}$ mM $NaH_2PO_4$ and 1 mM EDTA, pH 7.4.

DETAILED DESCRIPTION OF THE INVENTION

In yeast and other fungi, for example *C. albicans, Aspergillus nidulans, Aspergillus fumigatus, Cryptococcus neofomans, C. Krusei, C. parapsilosis, C. tropicalis,* and *C. glabrata,* IPC synthase catalyzes a step in the synthesis of inositolphosphoryl ceramide from ceramide and phosphatidylinositol (G. Becker and R. Lester, Biosynthesis of phosphoinositol-containing sphingolipid from phosphatidylinositol by a membrane prepartation from *Saccharomyces cervisiae. J. Bacteriol.* 142, 747–754, 1980). Sphingolipids are necessary for growth and viability of the yeast *S. cerevisiae.* Since IPC synthase is unique to fungi and plants it is a good target for antifungal therapy in mammals.

The IPC synthase gene of *C. glabrata* comprises the DNA sequence designated herein as SEQ ID NO 1. The IPC synthase gene of *C. Krusei* comprises the DNA sequence designated herein as SEQ ID NO 4. The IPC synthase gene of *C. parapsilosis* comprises the DNA sequence designated herein as SEQ ID NO 7. The IPC synthase gene of *C. tropicalis* comprises the DNA sequence designated herein as SEQ ID NO 10. The IPC synthase gene of *A. fumigatus* is designated herein as SEQ ID NO:13. The IPC synthase gene of *A. nidulans* is designated herein as SEQ ID NO:16. There are no intervening sequences in these genes. The IPC synthase gene of *C. neoformans* is designated herein as SEQ ID NO:19 and the cDNA thereof as SEQ ID NO:20. There is one intervening sequence in SEQ ID NO:19, from base pair 1888 through base pair 1939. Those skilled in the art will recognize that owing to the degeneracy of the genetic code (i.e. 64 codons which encode 20 amino acids), numerous "silent" substitutions of nucleotide base pairs could be introduced into these sequences without altering the identity of the encoded amino acid(s) or protein products. All such substitutions are intended to be within the scope of the invention. The genes disclosed and contemplated herein are useful for expressing the protein encoded thereby, in vitro or in a recombinant host cell.

Also contemplated is the use of said genes and fragments thereof as molecular hybridization probes for the identification and isolation of homologous genes.

Also contemplated by the present invention are nucleic acids that hybridize under high stringency conditions to the nucleic acid sequences disclosed herein.

Also contemplated are nucleic acids that are at least 70% identical in sequence to a nucleic acid sequence disclosed herein.

Gene Isolation Procedures

Those skilled in the art will recogize that the IPC synthase genes disclosed herein may be obtained by a plurality of applicable genetic and recombinant DNA techniques including, for example, polymerase chain reaction (PCR) amplification, or de novo DNA synthesis. (See e.g., J. Sambrook et al. *Molecular Cloning,* 2d Ed. Chap. 14 (1989)).

Skilled artisans will recognize that the IPC synthase genes disclosed herein, or fragments thereof, could be isolated by PCR amplification of genomic DNA isolated from suitable fungal cells using oligonucleotide primers targeted to any suitable region of SEQ ID NO:1, SEQ ID NO:4, SEQ ID NO:7, SEQ ID NO:10, SEQ ID NO:13, SEQ ID NO:16, or SEQ ID NO:19. The skilled artisan understands that the choice of suitable primers may involve routine experimentation to achieve a successful outcome in a PCR amplification and that some trial and error with specific primers may be necessary. Methods for PCR amplification are widely known in the art. See e.g. *PCR Protocols: A Guide to Method and Application,* Ed. M. Innis et al., Academic Press (1990). The PCR amplification reaction comprises genomic DNA, suitable enzymes, primers, and buffers, and is conveniently carried out in a DNA Thermal Cycler (Perkin Elmer Cetus, Norwalk, Conn.). A positive result is determined by detecting an appropriately-sized DNA fragment following agarose gel electrophoresis.

Protein Production Methods

One of the embodiments of the present invention relates to the purified proteins encoded by the IPC synthase genes disclosed herein, or functionally related proteins.

Skilled artisans will recognize that the proteins of the present invention can be synthesized by a variety of different methods. For example, the amino acid compounds of the invention can be made by chemical methods, well known in the art, including solid phase peptide synthesis or recombinant methods. Both methods are described in U.S. Pat. No. 4,617,149, which hereby is incorporated by reference.

Solid phase chemical synthetic methods for polypeptides are well known in the art, and are described in general texts covering the area. See, e.g., H. Dugas and C. Penney, *Bioorganic Chemistry* (1981) Springer-Verlag, New York, 54–92. For example, peptides may be synthesized by solid-phase methodology utilizing an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

The proteins of the present invention can also be produced by recombinant DNA methods using a cloned IPC synthase gene described herein. Recombinant methods are preferred if a high yield is desired. Expression of a cloned IPC synthase gene can be carried out in a variety of suitable host cells, well known to those skilled in the art. For this purpose, an IPC synthase gene is introduced into a host cell by any suitable means, well known to those skilled in the art. While chromosomal integration of the cloned IPC synthase gene is within the scope of the present invention, it is preferred that the gene be cloned into a suitable extra-chromosomally maintained expression vector so that the coding region of the IPC synthase gene is operably-linked to a constitutive or inducible promoter.

The basic steps in the recombinant production of the IPC synthase protein are:

a) constructing a natural, synthetic or semi-synthetic DNA encoding IPC synthase;

b) incorporating said DNA into an expression vector in a manner suitable for expressing an IPC synthase protein, either alone or as a fusion protein;

c) transforming an appropriate eucaryotic or prokaryotic host cell with said expression vector, d) culturing said transformed host cell in a manner to express the IPC synthase protein; and e) recovering membranes from said host cell and/or purifying the IPC synthase protein by any suitable means, well known to those skilled in the art.

Expressing Recombinant IPC synthase in Procaryotic and Eucaryotic Host Cells

In general, prokaryotes are used for cloning DNA sequences and for constructing the vectors of the present invention. Prokaryotes are also employed in the production of the IPC synthase protein. For example, the *Escherichia coli* K12 strain 294 (ATCC No. 31446) is particularly useful for expressing heterologous proteins in a procaryotic host. Other strains of *E. coli,* bacilli such as *Bacillus subtilis,* enterobacteriaceae such as *Salmonella typhimurium* or *Serratia marcescans,* various Pseudomonas species and other bacteria, such as Streptomyces, may also be employed as host cells in cloning and expressing the recombinant proteins of this invention.

Promoters that are suitable for driving expression of genes in prokaryotes include b-lactamase [e.g. vector pGX2907, ATCC 39344, contains a replicon and b-lactamase gene], lactose systems [Chang et al., Nature_(London), 275:615 (1978); Goeddel et al., Nature (London), 281:544 (1979)], alkaline phosphatase, and the tryptophan (trp) promoter system [vector pATH1 (ATCC 37695) which is designed to facilitate expression of an open reading frame as a trpE fusion protein under the control of the trp promoter]. Hybrid promoters such as the tac promoter (isolatable from plasmid pDR540, ATCC-37282) are also suitable. Still other bacterial promoters, whose nucleotide sequences are generally known, enable one of skill in the art to ligate such promoter sequences to DNA encoding the proteins of the instant invention using linkers or adapters to supply any required restriction sites. Promoters for use in bacterial systems also will contain a Shine-Dalgarno sequence operably-linked to the DNA encoding the desired polypeptides. These examples are illustrative rather than limiting.

The proteins of this invention may be synthesized either by direct expression or as a fusion protein comprising the protein of interest as a translational fusion with another protein or peptide, which may be removable by enzymatic or chemical cleavage. It is often observed in the production of certain peptides in recombinant systems that expression as a fusion protein prolongs the lifespan, increases the yield of the desired peptide, or provides a convenient means of purifying the protein. A variety of peptidases (e.g. enterokinase and thrombin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13, in *Protein Purification: From Molecular Mechanisms to Large Scale Processes,* American Chemical Society, Washington, D.C. (1990).

In addition to prokaryotes, mammalian host cells and eucaryotic microbes, such as yeast, may also be used to express the proteins of this invention. The simple eucaryote *Saccharomyces cerevisiae* is the most commonly used eucaryotic microorganism, although a number of other yeasts, such as *Kluyveromyces lactis,* are also suitable. For expression in Saccharomyces, the plasmid YRp7 (ATCC-40053), for example, may be used. See, e.g., D. Stinchcomb et al., *Nature,* 282:39 (1979); J. Kingsman et al., *Gene,* 7:141 (1979); S. Tschemper et al., *Gene,* 10:157 (1980). Plasmid YRp7 contains the TRP1 gene which provides a selectable marker for use in a trp1 auxotrophic mutant.

Purification of Recombinantly-Produced IPC synthase

An expression vector carrying a cloned IPC synthase gene or cDNA from any of the fungi disclosed herein (SEQ ID NO:1, SEQ ID NO:4, SEQ ID NO:7, SEQ ID NO:10, SEQ ID NO:13, SEQ ID NO:16, SEQ ID NO:19, or SEQ ID NO:20) is transformed or transfected into a suitable host cell using standard methods. Cells which contain the vector are propagated under conditions suitable for expression of the IPC synthase protein. If an IPC synthase gene is under the control of an inducible promoter then growth conditions would incorporate the appropriate inducer. The recombinantly-produced IPC synthase protein may be purified from cellular extracts of transformed cells by any suitable means. In a preferred method for protein purification, an IPC synthase gene used in transforming a host cell is modified at the 5' end to incorporate several histidine residues at the amino terminus of the encoded IPC synthase protein. This "histidine tag" enables a single-step protein purification method referred to as "immobilized metal ion affinity chromatography" (IMAC), essentially as described in U.S. Pat. No. 4,569,794, which hereby is incorporated by reference. The IMAC method enables rapid isolation of substantially pure protein.

IPC synthase activity can be detected in membranes from recombinant cells transformed with the genes disclosed herein, or in the membranes of non-transformed fungal cells that express said genes. Said membranes are a useful source of IPC synthase activity and can be used as a reagent in an assay for IPC synthase activity.

Other embodiments of the present invention relate to isolated nucleic acid sequences which encode SEQ ID NO:2, SEQ ID NO:5, SEQ ID NO:8, SEQ ID NO:11, SEQ ID NO:14, SEQ ID NO:17, or SEQ ID NO:21 or fragments thereof. As skilled artisans will recognize, the amino acid compounds of the invention can be encoded by a multitude of different nucleic acid sequences due to the degeneracy of the genetic code. Because these alternative nucleic acid sequences would encode the same amino acid sequences, the present invention further comprises these alternate nucleic acid sequences.

The IPC synthase genes comprising the present invention may be produced using synthetic methods well known in the art. See, e.g., E. L. Brown, R. Belagaje, M. J. Ryan, and H. G. Khorana, *Methods in Enzymology,* 68:109–151 (1979). The DNA segments corresponding to an IPC synthase gene could be generated using a conventional DNA synthesizing apparatus, such as the Applied Biosystems Model 380A or 380B DNA synthesizers (Applied Biosystems, Inc., 850 Lincoln Center Drive, Foster City, Calif. 94404) which employ phosphoramidite chemistry. Alternatively, phosphotriester chemistry may be employed to synthesize the nucleic acids of this invention. [See, e.g., M. J. Gait, ed., *Oligonucleotide Synthesis, A Practical Approach,* (1984).]

In an alternative method, IPC synthase DNA sequences comprising a portion or all of SEQ ID NO:1, SEQ ID NO:4, SEQ ID NO:7, SEQ ID NO:10, SEQ ID NO:13, SEQ ID NO:16, SEQ ID NO:19, or SEQ ID NO:20 can be generated from fungal genomic DNA using suitable oligonucleotide primers complementary to these sequences or region therein, utilizing the polymerase chain reaction as described in U.S. Pat. No. 4,889,818, which is incorporated herein by reference. Protocols for performing the PCR are disclosed in, *PCR Protocols: A Guide to Method and Applications,* Ed. Michael A. Innis et al., Academic Press, Inc. (1990), which hereby is incorporated by reference.

The ribonucleic acids of the present invention may be prepared using polynucleotide synthetic methods discussed supra, or they may be prepared enzymatically using RNA polymerases to transcribe a DNA template.

The most preferred system for preparing the ribonucleic acids of the present invention employs the RNA polymerase from the bacteriophage T7 or bacteriophage SP6. These RNA polymerases are highly specific and require the insertion of bacteriophage-specific sequences at the 5' end of the template to be transcribed. See, J. Sambrook, et al., supra, at 18.82–18.84.

This invention also provides nucleic acids, RNA or DNA, which are complementary to SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:18, SEQ ID NO:19, SEQ ID NO:20, or SEQ ID NO:22.

The present invention also provides probes and primers useful for molecular biology techniques. A compound that is SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:19, SEQ ID NO:20, or SEQ ID NO:22, or a complementary sequence thereof, or a fragment thereof, and which is at least 15 base pairs in length, and which will selectively hybridize to *C. glabrata, C. krusei, C. parapsilosis, C. tropicalis* or *C. neoformans* DNA or mRNA encoding IPC synthase, is provided. Preferably, the compound is DNA.

The probes and primers contemplated herein can be prepared enzymatically by well known methods (See e.g. Sambrook et al. supra).

Another aspect of the present invention relates to recombinant DNA cloning vectors and expression vectors comprising the nucleic acids described and contemplated herein. Many of the vectors encompassed within this invention are described above. The preferred nucleic acid vectors are those which comprise DNA. The most preferred recombinant DNA vectors comprise the isolated DNA sequences SEQ ID NO:1, SEQ ID NO:4, SEQ ID NO:7, SEQ ID NO:10, SEQ ID NO:13, SEQ ID NO:16, SEQ ID NO:19, or SEQ ID NO:20.

The skilled artisan understands that choosing the most appropriate cloning vector or expression vector depends upon a number of factors including the availability of appropriate restriction enzyme sites, the type of host cell into which the vector is to be transfected or transformed, the purpose of the transfection or transformation (e.g., stable transformation as an extrachromosomal element, or integration into the host chromosome), the presence or absence of readily assayable or selectable markers (e.g., antibiotic resistance markers, metabolic markers, or the like), and the number of copies of the gene to be present in the host cell.

Vectors suitable to carry the nucleic acids of the present invention include RNA viruses, DNA viruses, lytic bacteriophages, lysogenic bacteriophages, stable bacteriophages, plasmids, viroids, and the like. The most preferred vectors are plasmids.

When preparing an expression vector the skilled artisan understands that there are many variables to be considered, for example, whether to use a constitutive or inducible promoter. Inducible promoters are preferred because they may be the basis for high level and regulatable expression of an operably-linked gene. The skilled artisan will recognize a number of inducible promoters and inducers, for example, carbon source, metal ions, heat, and others known to the skilled artisan. The practitioner also understands that the amount of nucleic acid or protein to be produced dictates, in part, the selection of the expression system. The addition of certain nucleotide sequences, such as a sequence encoding a signal peptide preceding the coding sequence, is useful to direct localization of the resulting polypeptide.

Host cells harboring the nucleic acids disclosed herein are also provided by the present invention. A preferred host is *E. coli,* into which has been transfected or transformed a vector that comprises a nucleic acid of the present invention.

The present invention also provides a method for constructing a recombinant host cell capable of expressing SEQ ID NO:2, SEQ ID NO:5, SEQ ID NO:8, SEQ ID NO:11, SEQ ID NO:14, SEQ ID NO:17, or SEQ ID NO:21 said method comprising transforming a host cell with a recombinant DNA vector that comprises an isolated DNA sequence that encodes one of these sequences. Suitable host cells include any strain of *E. coli* or fungal cell that can accomodate high level expression of a gene(s) introduced by transformation or transfection. Preferred vectors for expression are those that comprise SEQ ID NO:1, SEQ ID NO:4, SEQ ID NO:7, SEQ ID NO:10, SEQ ID NO:13, SEQ ID NO:16, SEQ ID NO:19, or SEQ ID NO:20. Transformed host cells may be cultured under conditions well known to skilled artisans such that SEQ ID NO:2, SEQ ID NO:5, SEQ ID NO:8, SEQ ID NO:11, SEQ ID NO:14, SEQ ID NO:17, or SEQ ID NO:21 is expressed, thereby producing fungal IPC synthase protein in a recombinant host cell.

For the purpose of identifying or developing antifungal compounds, it would be desirable to determine those agents which inhibit IPC synthase activity. A method for determining whether a substance will inhibit the enzymatic reaction catalyzed by IPC synthase comprises contacting a source of IPC synthase activity (e.g. membrane preparation from a cell that expresses IPC synthase), or a purified IPC synthase protein, or fragment exhibiting said synthase activity, with a test substance and monitoring IPC synthase activity by any suitable means.

The instant invention provides such a screening system useful for discovering agents which inhibit an IPC synthase, said screening system comprising the steps of:

a) preparing a source of IPC synthase, or IPC synthase protein, or subunit thereof;

b) exposing said IPC synthase or source thereof to a test inhibitor;

c) introducing substrate; and d) quantifying the loss of activity of said IPC synthase.

Utilization of the screening system described above provides a means to determine compounds that may interfere with fungal sphingolipid biosynthesis. This screening system may be adapted to automated procedures such as a PANDEX® (Baxter-Dade Diagnostics) system allowing for efficient high-volume screening of potential therapeutic agents.

In such a screening protocol IPC synthase or subunit thereof is prepared as described herein, preferably using recombinant DNA technology. Alternatively, the reaction can be carried out using membranes from cells that express IPC synthase, as a source of IPC synthase activity. Preferably, the cells are recombinant cells that incorporate a recombinantly-expressed IPC synthase into the cell membrane. Most preferably, the recombinant cells are yeast cells. A sample of a test compound is then introduced into a reaction vessel containing IPC synthase activity, followed by the addition of enzyme substrate. Alternatively, substrate may be added simultaneously with the test compound.

The following examples more fully describe the present invention. Those skilled in the art will recognize that the particular reagents, equipment, and procedures described are merely illustrative and are not intended to limit the present invention in any manner.

EXAMPLE 1

Construction of a DNA Vector for Expressing the *C. glabrata* IPC synthase Gene in Homologous or Heterologous Host An expression vector suitable for expressing the IPC synthase gene of *C. glabrata* (SEQ ID NO:1) in *E. coli* contains an origin of replication (Ori), an ampicillin resistance gene (Amp) useful for selecting cells that have incorporated the vector following tranformation. The vector also includes the T7 promoter and T7 terminator sequences in operable linkage to the coding region of the IPC synthase gene. Parent plasmid pET11A (obtained from Novogen, Madison, Wisc.) is linearized by digestion with appropriate endonucleases and ligated to a DNA fragment comprising the coding region of the *C. glabrata* IPC synthase gene.

The IPC synthase gene ligated into the expression vector is modified at the 5' end (amino terminus of encoded protein) in order to simplify purification of the encoded IPC synthase protein product. For this purpose, an oligonucleotide encoding 8 histidine residues and a factor Xa cleavage site is inserted after the ATG start codon at nucleotide positions 1 to 3 of SEQ ID NO:1. Placement of the histidine residues at the amino terminus of the encoded protein enables the IMAC one-step protein purification procedure (See below).

EXAMPLE 2

Expression of *C. glabrata* IPC synthase Gene in *Echerichia coli* and Purification of IPC synthase Enzyme A plasmid from Example 1 is transformed into *E. coli* BL21 (DE3)(hsdS gal lcIts857 ind1Sam7nin5lacUV5-T7gene 1) using standard methods (See e.g. Sambrook et al. Supra). Transformants, selected for resistance to ampicillin, are chosen at random and tested for the presence of the vector by agarose gel electrophoresis using quick plasmid preparations. Colonies that contain the vector are grown, processed, and the protein encoded by the IPC synthase gene is purified by immobilized metal ion affinity chromatography (IMAC), essentially as described in U.S. Pat. No. 4,569,794, the entire contents of which is hereby incorporated by reference.

Briefly, the IMAC column is prepared as follows. A metal-free chelating resin (e.g. SEPHAROSE 6B IDA, Pharmacia) is washed in distilled water to remove preservative substances and infused with a suitable metal ion [e.g. Ni(II), Co(II), or Cu(II)] by adding a 50 mM metal chloride or metal sulfate aqueous solution until about 75% of the interstitial spaces of the resin is saturated with colored metal ion. The column is then ready to receive a crude cellular extract containing the IPC synthase protein product encoded by the vector.

After removing unbound proteins and other materials by washing the column with suitable buffer, pH 7.5, the bound protein is eluted in buffer at pH 4.3 essentially as described in U.S. Pat. No. 4,569,794.

EXAMPLE 3

Biochemical Assay for Inhibitors of IPC synthase Using Fungal Membrane Preparations The activity of the IPC synthase enzyme is assayed by preparing membranes from *C. glabrata,* for example, and using said membranes as a source of IPC synthase activity.

A suitable, rich medium, for example YEPD, is innoculated with a culture and allowed to grow overnight at room temperature with vigorous shaking. About 250 ml of fresh medium containing 20 μg/ml myo-inositol is innoculated with the overnight culture, and grown overnight at 30° C. Cells are harvested by centrifugation and resuspended in ice cold 50 mM potassium phosphate buffer, pH 7. Cells are washed twice in the same buffer and then resuspended in the same buffer containing 5 mM dithiothreitol (DTT), 1 μg/ml aprotinin, 0.6 μM leupeptin, 1 mM PMSF, and 1 μg/ml pepstatin A. Cells are ruptured using glass beads in a procedure that involves 5 successive vortexings each for 30 seconds followed by 2 to 5 minute intervals of rest on ice. Membranes are pelleted by centrifugation at 100,000 ×g for 1 hour at 4° C. The pellet is resuspended in cold buffer containing DTT and protease inhibitors and disrupted further by Dounce homogenization with 5 to 6 strokes on ice. Membranes are mixed with glycerol to a final concentration of 33% and stored frozen at −80° C. For use as "protein stock," thaw and dilute to 4.8 mg/ml in 0.05 M potassium phosphate(Kpi) buffer, pH 7.0 on ice.

IPC synthase is assayed by any suitable method. For example:

Final Assay Conditions:

5–50 μM NBD-C6-ceramide (from Molecular Probes)

1 mM phosphatidylinositol (Sigma-soybean)

2 mM CHAPS 50 mM potassium phosphate buffer, pH 7.0

Up to 2.5% organic co-solvent

Protein to 1.2 mg/ml

Final Vol. 100 μl

2X Master Mix (for 15 samples)

46 μl of 1 mg/ml NBD-C6-ceramide in MeOH

142 μl of 10 mg/ml phosphatidylinositol in $CHCl_3$

Dry under vacuum Redissolve by adding in order

160 μl 20 mM CHAPS

560 μl deionized water

80 μl 0.5 M Kpi buffer, pH 7.0

Sonicate 5 minutes.

Aliquot 50 μl of 2X master mix to screw cap microfuge at room temperature. Add 20 μl of 0.05 M Kpi buffer pH 7.0 to each sample followed by 5 μl of test compound or extract. The reaction is initiated by adding 25 μl of protein stock and incubating for 1 hour in a 30° C. water bath. Reactions are terminated by adding 900 μl of cold absolute methanol. Samples are stored at −20° C. for 1 hour and centrifuged at 14000 ×g at 4° C. for 30 minutes.

The reaction is monitored by HPLC on a Beckman Ultrasphere-ODS 5 μm, 150×4 mm column. The chromatogram is developed in 87% MeOH/13% 50 mM TEAP, pH 5.8, at a flow rate of 1 ml/min at room temperature through a Beckman Model 157 Fluorescence detector, using NBD-$C_6$-phosphatidylcholine as an internal standard.

Inhibition studies are carried out using the same reaction conditions described in the preceding paragraph. Compounds to be studied for inhibitory activity are added to final concentrations of between 1 pM and 10 mM.

EXAMPLE 4

Expression of *C. parapsilosis* (SEQ ID NO:7) IPC synthase Gene in *S. cerevisiae*

A yeast/*E.coli* shuttle vector suitable for expressing the *C. parapsilosis* IPC synthase gene (SEQ ID NO:7) in *S. cerevisiae* is constructed in parent plasmid YEp351 (See J. Hill et.al., *Yeast,* 2, 163–167, 1986), which contains the multiple cloning region of pUC18, the $Amp^R$ gene for selection in *E.coli,* 2μreplicon, and the LEU2 gene for selection in yeast. A fragment containing the *C.parapsilosis* IPC synthase gene is prepared by PCR amplification. Suitable primers to the 5' and 3' ends of the coding region disclosed in SEQ ID NO:7 are constructed to contain BamH1 cloning sites in addition to IPC synthase coding information. After PCR amplification of *C.parapsilosis* genomic DNA, the amplified fragment is purified by any sutiable method, for example, gel purification of an appropriately sized fragment, followed by treatment with restriction enzyme BamH1, and ligation to BamH1 digested YEp351. The recombinant plasmid carrying the IPC synthase gene is transformed into any suitable leu strain of *S. cerevisiae* and transformants selected for growth in a medium that lacks added leucine. Membranes from tranformants are prepared, and IPC synthase activity assayed as in Example 3.

SEQUENCE LISTING

```
<160> NUMBER OF SEQ ID NOS:  24

<210> SEQ ID NO 1
<211> LENGTH: 2000
<212> TYPE: DNA
<213> ORGANISM: Candida glabrata
<220> FEATURE:
<221> NAME/KEY: CDS
<222> LOCATION: (501)..(1748)

<400> SEQUENCE: 1

aaaacgtcat tttaaaatta ggctttagat tgtaactcag atgattttcg t caatccagt     60

gtacgaaact tggcaaatgc taaaacttca acaaataaat catcatccct a atactagtg    120

taaataattt aatgtacatg gtgttctatt tctaatgtag aaatatgtat a tgacattag    180

atcaactcat attgttcaaa actctgtcaa aataatttag tgaggcaaag g tgtcgtccc    240

ccgaatgaac ttgtaactca ccttgaagga gatatttgca tttacttgat a atccgaaac    300

ttttgcaact taacatttta aaactagaag ttatttggta tctggtatta a tttttatta    360

gctttgctga ttacgacacg ttacgaagga agatattgac gctcagaatt t ttatttagg    420

agaaatttat cataatagac aatatttgcc attaccgatt tctaactaaa t atcataatc    480

atagttatta gacaaattca atg aga ctt gga aga tgg t tt gct att ttg agc    533
                      Met Arg Leu Gly Arg Trp Phe Ala Ile Leu Ser
                        1               5                  10

tca aaa tta tgc tca gat aca gat gta act a ag ttg gag aga agt ctt      581
Ser Lys Leu Cys Ser Asp Thr Asp Val Thr L ys Leu Glu Arg Ser Leu
            15                  20                  25

gat gta agg gtc aca tta aga cga ctc agg a gt tac aga ccc aca ata      629
Asp Val Arg Val Thr Leu Arg Arg Leu Arg S er Tyr Arg Pro Thr Ile
        30                  35                  40
```

-continued

```
ggt gac aca gtt cat tat tca ttt ttg tca a tg att cta ttg tat tca      677
Gly Asp Thr Val His Tyr Ser Phe Leu Ser M et Ile Leu Leu Tyr Ser
     45                  50                  55

tat ttt gct aat cca cta cca ttc att gtg a aa aca ttg ata gcg atg      725
Tyr Phe Ala Asn Pro Leu Pro Phe Ile Val L ys Thr Leu Ile Ala Met
 60                  65                  70                  75

att tta atg act ctg ttt gtc gtc ccg atg a ca tct caa ttt ttc ttt      773
Ile Leu Met Thr Leu Phe Val Val Pro Met T hr Ser Gln Phe Phe Phe
                 80                  85                  90

aat gca ctt cca ata ttg aca tgg cta atc t tg tat ttt aca tca tca      821
Asn Ala Leu Pro Ile Leu Thr Trp Leu Ile L eu Tyr Phe Thr Ser Ser
             95                 100                 105

cat att cct aat agt cat aga cct tca att t ct gtt gag gtg ctt cct      869
His Ile Pro Asn Ser His Arg Pro Ser Ile S er Val Glu Val Leu Pro
        110                 115                 120

gcc att gaa act atc ctg tat ggc gat aac t ta agt gag att ttg gct      917
Ala Ile Glu Thr Ile Leu Tyr Gly Asp Asn L eu Ser Glu Ile Leu Ala
    125                 130                 135

gca tgg caa aat aca att cta gat atc cta g ct tgg att cca tat ggt      965
Ala Trp Gln Asn Thr Ile Leu Asp Ile Leu A la Trp Ile Pro Tyr Gly
140                 145                 150                 155

ctg ttt cac ttt ggc gca cca ttt gtg gtt g ca att gtt tta ttt ata     1013
Leu Phe His Phe Gly Ala Pro Phe Val Val A la Ile Val Leu Phe Ile
                160                 165                 170

ttt gga cca ccg aca gtt ctt cag ggt tat g cg ttt gcg ttt ggt tat     1061
Phe Gly Pro Pro Thr Val Leu Gln Gly Tyr A la Phe Ala Phe Gly Tyr
            175                 180                 185

gtg aat tta ttt ggg gtg tta ttc caa aac a ta ttt ccc gcc gcg gct     1109
Val Asn Leu Phe Gly Val Leu Phe Gln Asn I le Phe Pro Ala Ala Ala
        190                 195                 200

cct tgg tat aaa ata cat tat gga ctc caa g tt gca aat tac agt atc     1157
Pro Trp Tyr Lys Ile His Tyr Gly Leu Gln V al Ala Asn Tyr Ser Ile
    205                 210                 215

aaa ggt atg cct ggt gga ctt tct aga att g at gat ctt ttg ggt gtg     1205
Lys Gly Met Pro Gly Gly Leu Ser Arg Ile A sp Asp Leu Leu Gly Val
220                 225                 230                 235

aat tta tat tca agt ggt ttt aag aac tct g ct gtc gtt ttt gga gct     1253
Asn Leu Tyr Ser Ser Gly Phe Lys Asn Ser A la Val Val Phe Gly Ala
                240                 245                 250

ttt cct tct ctt cat tct gca tgt gca act a tg gaa gca ctc ttc ttc     1301
Phe Pro Ser Leu His Ser Ala Cys Ala Thr M et Glu Ala Leu Phe Phe
            255                 260                 265

tca tat tgt ttt cca agc ttg aca ccg ctc t tt att ttc tac gtt tgg     1349
Ser Tyr Cys Phe Pro Ser Leu Thr Pro Leu P he Ile Phe Tyr Val Trp
        270                 275                 280

tgg tta tgg tgg tct aca atg tat ctt act c at cat tat ttt gtt gat     1397
Trp Leu Trp Trp Ser Thr Met Tyr Leu Thr H is His Tyr Phe Val Asp
    285                 290                 295

cta aca gca ggt tct gtt ttg gct tat ttc a ta ttt caa tat acc aaa     1445
Leu Thr Ala Gly Ser Val Leu Ala Tyr Phe I le Phe Gln Tyr Thr Lys
300                 305                 310                 315

tac aca cat cta cct att gtt gat cca aat c tg ctc ttc cgt tgg tcc     1493
Tyr Thr His Leu Pro Ile Val Asp Pro Asn L eu Leu Phe Arg Trp Ser
                320                 325                 330

tac gac agt att gaa ttt tac gat gtt aag a ac aat gac cct tta tcc     1541
Tyr Asp Ser Ile Glu Phe Tyr Asp Val Lys A sn Asn Asp Pro Leu Ser
            335                 340                 345

att aca aat aac gat ata gag agt ata cct c ta aac acc att gaa cta     1589
Ile Thr Asn Asn Asp Ile Glu Ser Ile Pro L eu Asn Thr Ile Glu Leu
        350                 355                 360
```

-continued

```
gat aca gaa gaa gtg ttc aat att gag cgg g aa aaa tct agg aca cca     1637
Asp Thr Glu Glu Val Phe Asn Ile Glu Arg G lu Lys Ser Arg Thr Pro
    365                 370                 375

gaa ttg tca cat gca gtg tct tca tct tct c ta gct aac ggt cgc tct     1685
Glu Leu Ser His Ala Val Ser Ser Ser Ser L eu Ala Asn Gly Arg Ser
380                 385                 390                 395

caa aca tat cca aat act gga aat aca ttc a aa tcc aag aca aga ctg     1733
Gln Thr Tyr Pro Asn Thr Gly Asn Thr Phe L ys Ser Lys Thr Arg Leu
                400                 405                 410

agt aaa ctg gtc att taaaaccagt atttataaat agagacta tc ttcttctact     1788
Ser Lys Leu Val Ile
            415

gtacatacaa tgatctttct atattctaac gaaatcaata agtgcatact a tattcattt   1848

aacatgatca atattattta acagatccat taggtgctgg cttcccaaga t agttaccaa   1908

aacgataatt ttttctcaaa atttgccctt tgagaaaaac ctccgtctag t caccccttta   1968

ccacacagca caaactgaaa atcgatggga ta                                  2000


<210> SEQ ID NO 2
<211> LENGTH: 416
<212> TYPE: PRT
<213> ORGANISM: Candida glabrata

<400> SEQUENCE: 2

Met Arg Leu Gly Arg Trp Phe Ala Ile Leu S er Ser Lys Leu Cys Ser
  1               5                  10                  15

Asp Thr Asp Val Thr Lys Leu Glu Arg Ser L eu Asp Val Arg Val Thr
             20                  25                  30

Leu Arg Arg Leu Arg Ser Tyr Arg Pro Thr I le Gly Asp Thr Val His
         35                  40                  45

Tyr Ser Phe Leu Ser Met Ile Leu Leu Tyr S er Tyr Phe Ala Asn Pro
     50                  55                  60

Leu Pro Phe Ile Val Lys Thr Leu Ile Ala M et Ile Leu Met Thr Leu
 65                  70                  75                  80

Phe Val Val Pro Met Thr Ser Gln Phe Phe P he Asn Ala Leu Pro Ile
                 85                  90                  95

Leu Thr Trp Leu Ile Leu Tyr Phe Thr Ser S er His Ile Pro Asn Ser
            100                 105                 110

His Arg Pro Ser Ile Ser Val Glu Val Leu P ro Ala Ile Glu Thr Ile
        115                 120                 125

Leu Tyr Gly Asp Asn Leu Ser Glu Ile Leu A la Ala Trp Gln Asn Thr
    130                 135                 140

Ile Leu Asp Ile Leu Ala Trp Ile Pro Tyr G ly Leu Phe His Phe Gly
145                 150                 155                 160

Ala Pro Phe Val Val Ala Ile Val Leu Phe I le Phe Gly Pro Pro Thr
                165                 170                 175

Val Leu Gln Gly Tyr Ala Phe Ala Phe Gly T yr Val Asn Leu Phe Gly
            180                 185                 190

Val Leu Phe Gln Asn Ile Phe Pro Ala Ala A la Pro Trp Tyr Lys Ile
        195                 200                 205

His Tyr Gly Leu Gln Val Ala Asn Tyr Ser I le Lys Gly Met Pro Gly
    210                 215                 220

Gly Leu Ser Arg Ile Asp Asp Leu Leu Gly V al Asn Leu Tyr Ser Ser
225                 230                 235                 240

Gly Phe Lys Asn Ser Ala Val Val Phe Gly A la Phe Pro Ser Leu His
```

-continued

```
                245                 250                 255

Ser Ala Cys Ala Thr Met Glu Ala Leu Phe P he Ser Tyr Cys Phe Pro
            260                 265                 270

Ser Leu Thr Pro Leu Phe Ile Phe Tyr Val T rp Trp Leu Trp Trp Ser
        275                 280                 285

Thr Met Tyr Leu Thr His His Tyr Phe Val A sp Leu Thr Ala Gly Ser
    290                 295                 300

Val Leu Ala Tyr Phe Ile Phe Gln Tyr Thr L ys Tyr Thr His Leu Pro
305                 310                 315                 320

Ile Val Asp Pro Asn Leu Leu Phe Arg Trp S er Tyr Asp Ser Ile Glu
                325                 330                 335

Phe Tyr Asp Val Lys Asn Asn Asp Pro Leu S er Ile Thr Asn Asn Asp
            340                 345                 350

Ile Glu Ser Ile Pro Leu Asn Thr Ile Glu L eu Asp Thr Glu Glu Val
        355                 360                 365

Phe Asn Ile Glu Arg Glu Lys Ser Arg Thr P ro Glu Leu Ser His Ala
    370                 375                 380

Val Ser Ser Ser Ser Leu Ala Asn Gly Arg S er Gln Thr Tyr Pro Asn
385                 390                 395                 400

Thr Gly Asn Thr Phe Lys Ser Lys Thr Arg L eu Ser Lys Leu Val Ile
                405                 410                 415


<210> SEQ ID NO 3
<211> LENGTH: 1248
<212> TYPE: RNA
<213> ORGANISM: Candida glabrata

<400> SEQUENCE: 3

augagacuug gaagaugguu ugcuauuuug agcucaaaau uaugcucaga u acagaugua     60

acuaaguugg agagaagucu ugauguaagg gucacauuaa gacgacucag g aguuacaga    120

cccacaauag gugacacagu ucauuauuca uuuuugucaa ugauucuauu g uauucauau    180

uuugcuaauc cacuaccauu cauugugaaa acauugauag cgaugauuuu a augacucug    240

uuugucgucc cgaugacauc ucaauuuuuc uuuaaugcac uuccaauauu g acauggcua    300

aucuuguauu uuacaucauc acauauuccu aauagucaua gaccuucaau u ucuguugag    360

gugcuuccug ccauugaaac uauccuguau ggcgauaacu uaagugagau u uuggcugca    420

uggcaaaaua caauucuaga uauccuagcu uggauuccau auggucuguu u cacuuuggc    480

gcaccauuug ugguugcaau uguuuuauuu auauuuggac caccgacagu u cuucagggu    540

uaugcguuug cguuugguua ugugaauuua uuuggggugu uauuccaaaa c auauuuccc    600

gccgcggcuc cuugguauaa aauacauuau ggacuccaag uugcaaauua c aguaucaaa    660

gguaugccug guggacuuuc uagaauugau gaucuuuugg gugugaauuu a uauucaagu    720

gguuuuaaga acucugcugu cguuuuugga gcuuuuccuu cucuucauuc u gcaugugca    780

acuauggaag cacucuucuu cucauauugu uuuccaagcu ugacaccgcu c uuuauuuuc    840

uacguuuggu gguuauggug gucuacaaug uaucuuacuc aucauuauuu u guugaucua    900

acagcagguu cuguuuuggc uuauuucaua uuucaauaua ccaaauacac a caucuaccu    960

auuguugauc caaaucugcu cuuccguugg uccuacgaca guauugaauu u uacgauguu   1020

aagaacaaug acccuuuauc cauuacaaau aacgauauag agaguauacc u cuaaacacc   1080

auugaacuag auacagaaga aguguucaau auugagcggg aaaaaucuag g acaccagaa   1140

uugucacaug cagugucuuc aucuucucua gcuaacgguc gcucucaaac a uauccaaau   1200
```

-continued

```
acuggaaaua cauucaaauc caagacaaga cugaguaaac uggucauu                1248


<210> SEQ ID NO 4
<211> LENGTH: 2000
<212> TYPE: DNA
<213> ORGANISM: Candida kruisii
<220> FEATURE:
<221> NAME/KEY: CDS
<222> LOCATION: (300)..(1739)

<400> SEQUENCE: 4

acagtaaaaa gaaattgcgc tgcatgaaac tttttttttt tttttttcg g tgtttcttc     60

tcgtttttct cgtttttctc gtttttctcg gtttcttttg agaatgtaat g aaatttgga    120

aactgtacaa acattctcag tgttgatatt aacaataata accacattga c attgacaac    180

atcattatta ggttctttcc atttgtatta tttccatctc ggacacgtca g ctatagacc    240

gtcgacactc cctattccct gcaccaacta ggaagaacag gaagaacaag a agaacaga     299

atg ctc tcg ctc ccg gcc ctt att agg cgc c tg tat tcc tcc ttt att      347
Met Leu Ser Leu Pro Ala Leu Ile Arg Arg L eu Tyr Ser Ser Phe Ile
  1               5                  10                  15

tcg gca aga gaa aag ggt aat tca ttg cct g ca tta aag aca tcc ttt      395
Ser Ala Arg Glu Lys Gly Asn Ser Leu Pro A la Leu Lys Thr Ser Phe
             20                  25                  30

aac ccc ctc cct aac ttc aag acc ttc ccg g ag aga ctg gtc tcg gca      443
Asn Pro Leu Pro Asn Phe Lys Thr Phe Pro G lu Arg Leu Val Ser Ala
         35                  40                  45

tcc ata tcc aat gtg gtc cat ttc acg att a tc ttt ctt gtc ttt gtc      491
Ser Ile Ser Asn Val Val His Phe Thr Ile I le Phe Leu Val Phe Val
     50                  55                  60

ttc tcc atc tca ata atg cct gta ccc cta c tt gtg aaa gcc att ctt      539
Phe Ser Ile Ser Ile Met Pro Val Pro Leu L eu Val Lys Ala Ile Leu
 65                  70                  75                  80

atc att gtc ttg att tac atc aac ttt gct c ca att ttc gcc cag ttc      587
Ile Ile Val Leu Ile Tyr Ile Asn Phe Ala P ro Ile Phe Ala Gln Phe
                 85                  90                  95

ttt aac ggc ggc ttg ccg atc ctc tca tgg g tc att ttg ttc ttt aac      635
Phe Asn Gly Gly Leu Pro Ile Leu Ser Trp V al Ile Leu Phe Phe Asn
            100                 105                 110

tca aag aac ata cct ctg tca atg aag aga c cc atc tcc gtc aag gtc      683
Ser Lys Asn Ile Pro Leu Ser Met Lys Arg P ro Ile Ser Val Lys Val
        115                 120                 125

ttg ccc gca ttg gag aca atc ttc tat ggc g at aat tta tct gaa atc      731
Leu Pro Ala Leu Glu Thr Ile Phe Tyr Gly A sp Asn Leu Ser Glu Ile
    130                 135                 140

ttg gct tct cat aca aac act ttc ttg gac t tg ttt gct tgg ttc cca      779
Leu Ala Ser His Thr Asn Thr Phe Leu Asp L eu Phe Ala Trp Phe Pro
145                 150                 155                 160

tat ggt ata gtc cat ttc tcc ctg ccc ttt g tt gtg gca gcc ctt att      827
Tyr Gly Ile Val His Phe Ser Leu Pro Phe V al Val Ala Ala Leu Ile
                165                 170                 175

ttt tta ttt gcc ccc cct aaa acc tta ccc c aa ttt tgt tgg tcc ttt      875
Phe Leu Phe Ala Pro Pro Lys Thr Leu Pro G ln Phe Cys Trp Ser Phe
            180                 185                 190

ggt tat atg aat ttg gtt ggc gtc att atc c aa aac ttg gtt ttc tca      923
Gly Tyr Met Asn Leu Val Gly Val Ile Ile G ln Asn Leu Val Phe Ser
        195                 200                 205

tgt gct cca cca tgg tat aaa gtg ctg cat g gg ttg gac aag gca aac      971
Cys Ala Pro Pro Trp Tyr Lys Val Leu His G ly Leu Asp Lys Ala Asn
    210                 215                 220
```

-continued

```
tat tca atg aag gga tcg cca gga gga ttg g gt aga atc gat gga ctg     1019
Tyr Ser Met Lys Gly Ser Pro Gly Gly Leu G ly Arg Ile Asp Gly Leu
225                 230                 235                 240

ttt ggt ttc gat atg tac acc tcg ggt ttc a cc aat tct ccc ttg att     1067
Phe Gly Phe Asp Met Tyr Thr Ser Gly Phe T hr Asn Ser Pro Leu Ile
                245                 250                 255

ttc ggt gca atg ccc tcc ttg cat tcg gga t gt tca act atg gac gca     1115
Phe Gly Ala Met Pro Ser Leu His Ser Gly C ys Ser Thr Met Asp Ala
            260                 265                 270

tta tgg ttg tct tat cta ttc cct aaa ttc a cc cct cta ttt gtt ttc     1163
Leu Trp Leu Ser Tyr Leu Phe Pro Lys Phe T hr Pro Leu Phe Val Phe
        275                 280                 285

tac gtt tgc tgg tta tgg ttc tct aca atg t at ttg act cat cat tac     1211
Tyr Val Cys Trp Leu Trp Phe Ser Thr Met T yr Leu Thr His His Tyr
    290                 295                 300

ttc atc gat gtt gtt gtt ggt tct tgt ttg g ca att gga ttc ttc act     1259
Phe Ile Asp Val Val Val Gly Ser Cys Leu A la Ile Gly Phe Phe Thr
305                 310                 315                 320

gca gtc aaa tgg aga ggc aga tta ccc gta a at gat cta ttt tgt agg     1307
Ala Val Lys Trp Arg Gly Arg Leu Pro Val A sn Asp Leu Phe Cys Arg
                325                 330                 335

tgg gac cat gat acc ctg aaa ttc cat gac a tt tgg aac gag gac cca     1355
Trp Asp His Asp Thr Leu Lys Phe His Asp I le Trp Asn Glu Asp Pro
            340                 345                 350

ctg agg gag aac tat ccc ttg gac ttg gag t ct tca aaa gac ttg gaa     1403
Leu Arg Glu Asn Tyr Pro Leu Asp Leu Glu S er Ser Lys Asp Leu Glu
        355                 360                 365

aat cag ata cct ttg agt gat ttg aat tca t ca tgt gat gaa caa cca     1451
Asn Gln Ile Pro Leu Ser Asp Leu Asn Ser S er Cys Asp Glu Gln Pro
    370                 375                 380

agt tca cca aag gga ttt aat agg aac cag a at aat aac ttg ggt gat     1499
Ser Ser Pro Lys Gly Phe Asn Arg Asn Gln A sn Asn Asn Leu Gly Asp
385                 390                 395                 400

aag gga cag gga tta gaa caa gta gac gat c aa gga gaa gaa tat gac     1547
Lys Gly Gln Gly Leu Glu Gln Val Asp Asp G ln Gly Glu Glu Tyr Asp
                405                 410                 415

aat tac gat ttt gat gat tct gat gac gac c aa att gct gaa gct aat     1595
Asn Tyr Asp Phe Asp Asp Ser Asp Asp Asp G ln Ile Ala Glu Ala Asn
            420                 425                 430

gat gtg gag aaa tcg gct aac aaa aca ata a ag aag act cca aag tca     1643
Asp Val Glu Lys Ser Ala Asn Lys Thr Ile L ys Lys Thr Pro Lys Ser
        435                 440                 445

tac aag gaa tca ttc gaa gca aca tta tct a ca aac ttg aac tca caa     1691
Tyr Lys Glu Ser Phe Glu Ala Thr Leu Ser T hr Asn Leu Asn Ser Gln
    450                 455                 460

att aca aat ttc cca tct tcc act cat ata c ct ctt aat tcc agt cgt     1739
Ile Thr Asn Phe Pro Ser Ser Thr His Ile P ro Leu Asn Ser Ser Arg
465                 470                 475                 480

tgacacaaac tcggttcttt aataactacc acttcgccct ttacttagcg t ctttgaaat   1799

tatagatctg gaattagaaa taaactacct tttttttgg ccaattggaa a aatttaata    1859

caactcttat caagtcactc ctttattttc aatctttttc tttatgtaca t gtaatttta   1919

cagagttcaa tagttaatta tttaattact tattttcact ttatagttac a ctcttctcc   1979

ccacgtcctt ttttcttatc a                                              2000
```

<210> SEQ ID NO 5
<211> LENGTH: 480
<212> TYPE: PRT

-continued

<213> ORGANISM: Candida kruisii

<400> SEQUENCE: 5

Met Leu Ser Leu Pro Ala Leu Ile Arg Arg L eu Tyr Ser Ser Phe Ile
1 5 10 15

Ser Ala Arg Glu Lys Gly Asn Ser Leu Pro A la Leu Lys Thr Ser Phe
20 25 30

Asn Pro Leu Pro Asn Phe Lys Thr Phe Pro G lu Arg Leu Val Ser Ala
35 40 45

Ser Ile Ser Asn Val Val His Phe Thr Ile I le Phe Leu Val Phe Val
50 55 60

Phe Ser Ile Ser Ile Met Pro Val Pro Leu L eu Val Lys Ala Ile Leu
65 70 75 80

Ile Ile Val Leu Ile Tyr Ile Asn Phe Ala P ro Ile Phe Ala Gln Phe
85 90 95

Phe Asn Gly Gly Leu Pro Ile Leu Ser Trp V al Ile Leu Phe Phe Asn
100 105 110

Ser Lys Asn Ile Pro Leu Ser Met Lys Arg P ro Ile Ser Val Lys Val
115 120 125

Leu Pro Ala Leu Glu Thr Ile Phe Tyr Gly A sp Asn Leu Ser Glu Ile
130 135 140

Leu Ala Ser His Thr Asn Thr Phe Leu Asp L eu Phe Ala Trp Phe Pro
145 150 155 160

Tyr Gly Ile Val His Phe Ser Leu Pro Phe V al Val Ala Ala Leu Ile
165 170 175

Phe Leu Phe Ala Pro Pro Lys Thr Leu Pro G ln Phe Cys Trp Ser Phe
180 185 190

Gly Tyr Met Asn Leu Val Gly Val Ile Ile G ln Asn Leu Val Phe Ser
195 200 205

Cys Ala Pro Pro Trp Tyr Lys Val Leu His G ly Leu Asp Lys Ala Asn
210 215 220

Tyr Ser Met Lys Gly Ser Pro Gly Gly Leu G ly Arg Ile Asp Gly Leu
225 230 235 240

Phe Gly Phe Asp Met Tyr Thr Ser Gly Phe T hr Asn Ser Pro Leu Ile
245 250 255

Phe Gly Ala Met Pro Ser Leu His Ser Gly C ys Ser Thr Met Asp Ala
260 265 270

Leu Trp Leu Ser Tyr Leu Phe Pro Lys Phe T hr Pro Leu Phe Val Phe
275 280 285

Tyr Val Cys Trp Leu Trp Phe Ser Thr Met T yr Leu Thr His His Tyr
290 295 300

Phe Ile Asp Val Val Val Gly Ser Cys Leu A la Ile Gly Phe Phe Thr
305 310 315 320

Ala Val Lys Trp Arg Gly Arg Leu Pro Val A sn Asp Leu Phe Cys Arg
325 330 335

Trp Asp His Asp Thr Leu Lys Phe His Asp I le Trp Asn Glu Asp Pro
340 345 350

Leu Arg Glu Asn Tyr Pro Leu Asp Leu Glu S er Ser Lys Asp Leu Glu
355 360 365

Asn Gln Ile Pro Leu Ser Asp Leu Asn Ser S er Cys Asp Glu Gln Pro
370 375 380

Ser Ser Pro Lys Gly Phe Asn Arg Asn Gln A sn Asn Asn Leu Gly Asp
385 390 395 400

-continued

```
Lys Gly Gln Gly Leu Glu Gln Val Asp Asp G ln Gly Glu Glu Tyr Asp
                405                 410                 415

Asn Tyr Asp Phe Asp Asp Ser Asp Asp Asp G ln Ile Ala Glu Ala Asn
            420                 425                 430

Asp Val Glu Lys Ser Ala Asn Lys Thr Ile L ys Lys Thr Pro Lys Ser
        435                 440                 445

Tyr Lys Glu Ser Phe Glu Ala Thr Leu Ser T hr Asn Leu Asn Ser Gln
    450                 455                 460

Ile Thr Asn Phe Pro Ser Ser Thr His Ile P ro Leu Asn Ser Ser Arg
465                 470                 475                 480


<210> SEQ ID NO 6
<211> LENGTH: 2000
<212> TYPE: RNA
<213> ORGANISM: Candida kruisii

<400> SEQUENCE: 6

acaguaaaaa gaaauugcgc ugcaugaaac uuuuuuuuuu uuuuuuuucg g uguuucuuc     60

ucguuuuucu cguuuuucuc guuuuucucg guuucuuuug agaauguaau g aaauuugga    120

aacuguacaa acauucucag uguugauauu aacaauaaua accacauuga c auugacaac    180

aucauuauua gguucuuucc auuuguauua uuuccaucuc ggacacguca g cuauagacc    240

gucgacacuc ccuauucccu gcaccaacua ggaagaacag gaagaacaag a agaacagaa    300

ugcucucgcu cccggcccuu auuaggcgcc uguauuccuc cuuuauuucg g caagagaaa    360

aggguaauuc auugccugca uuaaagacau ccuuuaaccc ccucccuaac u ucaagaccu    420

ucccggagag acuggucucg gcauccauau ccaauguggu ccauuucacg a uuaucuuuc    480

uugucuuugu cuucuccauc ucaauaaugc cuguaccccu acuugugaaa g ccauucuua    540

ucauugucuu gauuuacauc aacuuugcuc caauuuucgc ccaguucuuu a acggcggcu    600

ugccgauccu cucaugggguc auuuuguucu uuaacucaaa gaacauaccu c ugucaauga    660

agagacccau cuccgucaag gucuugcccg cauuggagac aaucuucuau g gcgauaauu    720

uaucugaaau cuuggcuucu cauacaaaca cuuucuugga cuuguuugcu u gguucccau    780

augguauagu ccauuucucc cugcccuuug uuguggcagc ccuuauuuuu u uauuugccc    840

ccccuaaaac cuuaccccaa uuuuguuggu ccuuugguua uaugaauuug g uuggcguca    900

uuauccaaaa cuugguuuuc ucaugugcuc caccauggua uaaagugcug c augggguugg    960

acaaggcaaa cuauucaaug aagggaucgc caggaggauu ggguagaauc g auggacugu   1020

uugguuucga uauguacacc ucggguuuca ccaauucucc cuugauuuuc g gugcaaugc   1080

ccuccuugca uucgggaugu ucaacuaugg acgcauuaug guugucuuau c uauucccua   1140

aauucacccc ucuauuuguu uucuacguuu gcugguuaug guucucuaca a uguauuuga   1200

cucaucauua cuucaucgau guuguuguug guucuuguuu ggcaauugga u ucuucacug   1260

cagucaaaug gagaggcaga uuacccguaa augaucuauu uuguaggugg g accaugaua   1320

cccugaaauu ccaugacauu uggaacgagg acccacugag ggagaacuau c ccuuggacu   1380

uggagucuuc aaaagacuug gaaaaucaga uaccuuugag ugauuugaau u caucaugug   1440

augaacaacc aaguucacca aagggauuua auaggaacca gaauaauaac u ugggugaua   1500

agggacaggg auuagaacaa guagacgauc aaggagaaga auaugacaau u acgauuuug   1560

augauucuga ugacgaccaa auugcugaag cuaaugaugu ggagaaaucg g cuaacaaaa   1620

caauaaagaa gacuccaaag ucauacaagg aaucauucga agcaacauua u cuacaaacu   1680
```

-continued

```
ugaacucaca aauuacaaau uucccaucuu ccacucauau accucuuaau u ccagucguu   1740

gacacaaacu cgguucuuua auaacuacca cuucgcccuu uacuuagcgu c uuugaaauu   1800

auagaucugg aauuagaaau aaacuaccuu uuuuuuuggc caauuggaaa a auuuaauac   1860

aacucuuauc aagucacucc uuuauuuuca aucuuuuucu uuauguacau g uaauuuuac   1920

agaguucaau aguuaauuau uuaauuacuu auuuucacuu uauaguuaca c ucuucuccc   1980

cacguccuuu uuucuuauca                                              200 0


<210> SEQ ID NO 7
<211> LENGTH: 1949
<212> TYPE: DNA
<213> ORGANISM: Candida parapsilosis
<220> FEATURE:
<221> NAME/KEY: CDS
<222> LOCATION: (162)..(1679)

<400> SEQUENCE: 7

cacacacaca cacgggttag agcatctgaa cttcacgaca actgttttct g tacaaccaa     60

aacaaaccac aacacaagac aacacaacac agtactttgc tgacattcaa t accaatacc    120

cgtctttttt ttttcaccac acaacgatat tgctttgaag g atg tca  cgc act tac    176
                                              Met Ser Arg Thr Tyr
                                                1               5

aat ggg tct tcc tcc tca tca ata ttt ctg a aa cca cgt cga ttt ttc      224
Asn Gly Ser Ser Ser Ser Ser Ile Phe Ser L ys Pro Arg Arg Phe Phe
                 10                  15                  20

aat aac tac ttt cta ctg gaa aaa tca cca a ct tca aca tta cct gat      272
Asn Asn Tyr Phe Leu Ser Glu Lys Ser Pro T hr Ser Thr Leu Pro Asp
             25                  30                  35

tta gaa aca aac act agc atc aga act agt c tt cat aga cta aga cat      320
Leu Glu Thr Asn Thr Ser Ile Arg Thr Ser L eu His Arg Leu Arg His
         40                  45                  50

cac aaa ttc ata aag gga gag att tta cac t at ggg ttt ctt tct ttt      368
His Lys Phe Ile Lys Gly Glu Ile Leu His T yr Gly Phe Leu Ser Phe
     55                  60                  65

gtt tgg tta ttt gtc ttt acc ata tac cca g ca tcc atc ttg ttt aaa      416
Val Trp Leu Phe Val Phe Thr Ile Tyr Pro A la Ser Ile Leu Phe Lys
 70                  75                  80                  85

att cca gtt tta ctt gca ttg cta acc att a tt act att cca gca act      464
Ile Pro Val Leu Leu Ala Leu Leu Thr Ile I le Thr Ile Pro Ala Thr
                 90                  95                 100

tca caa ttt ttt tta cca gca ctt ccc att t tg act tgg ttg ggt ttt      512
Ser Gln Phe Phe Leu Pro Ala Leu Pro Ile L eu Thr Trp Leu Gly Phe
            105                 110                 115

tac ttc act agt tcc aaa ata cct cat tct t gg aaa cca gct att tca      560
Tyr Phe Thr Ser Ser Lys Ile Pro His Ser T rp Lys Pro Ala Ile Ser
        120                 125                 130

gtc aag gtt tta cca gcc atg gag act atc t tg tat ggt gat gat tta      608
Val Lys Val Leu Pro Ala Met Glu Thr Ile L eu Tyr Gly Asp Asp Leu
    135                 140                 145

tca aat gta ttg gca acc atc act aac cgt g gt ttg gat att ttg ggc      656
Ser Asn Val Leu Ala Thr Ile Thr Asn Arg G ly Leu Asp Ile Leu Gly
150                 155                 160                 165

tgg tta cct tat ggt tta ttt cat ttt ggt g ct cca ttt gtt gta gct      704
Trp Leu Pro Tyr Gly Leu Phe His Phe Gly A la Pro Phe Val Val Ala
                170                 175                 180

gca att atg ttt ttc ttt gct cca cca act a gt tta aga tca ttt gcg      752
Ala Ile Met Phe Phe Phe Ala Pro Pro Thr S er Leu Arg Ser Phe Ala
            185                 190                 195
```

-continued

```
ttt gct ttt ggt tat atg aac ttg ttt ggg g tt att att caa atg atg      800
Phe Ala Phe Gly Tyr Met Asn Leu Phe Gly V al Ile Ile Gln Met Met
        200                 205                 210

ttt cca gct gct cca cct tgg tac aag aat t tg tat gga tta caa cca      848
Phe Pro Ala Ala Pro Pro Trp Tyr Lys Asn L eu Tyr Gly Leu Gln Pro
    215                 220                 225

gcc aac tat acc atg cat ggc tca cca ggt g ga ttg ggc cgt ata gat      896
Ala Asn Tyr Thr Met His Gly Ser Pro Gly G ly Leu Gly Arg Ile Asp
230                 235                 240                 245

gaa tta ttg gga gtc gat atg tac acc act g gg ttc tcc aac tca ccg      944
Glu Leu Leu Gly Val Asp Met Tyr Thr Thr G ly Phe Ser Asn Ser Pro
                250                 255                 260

gtt att ttt ggt gct ttc cca tca tta cat t ca ggt tgt tgt att atg      992
Val Ile Phe Gly Ala Phe Pro Ser Leu His S er Gly Cys Cys Ile Met
            265                 270                 275

gag gtt ttg ttt atg tgt tgg tta ttt ccc c gt ttg aaa gta ctt tgg     1040
Glu Val Leu Phe Met Cys Trp Leu Phe Pro A rg Leu Lys Val Leu Trp
        280                 285                 290

gtg ttt tat gca tct tgg tta tgg tgg agt a ca atg tac ttg act cat     1088
Val Phe Tyr Ala Ser Trp Leu Trp Trp Ser T hr Met Tyr Leu Thr His
    295                 300                 305

cac tat ttt gtt gat tta act ggt ggt gct g ta tta tca ttg gtt gtt     1136
His Tyr Phe Val Asp Leu Thr Gly Gly Ala V al Leu Ser Leu Val Val
310                 315                 320                 325

ttt gaa ttt gtc aag ttt aaa tac cta cct a ag gct aac aag cgt tgt     1184
Phe Glu Phe Val Lys Phe Lys Tyr Leu Pro L ys Ala Asn Lys Arg Cys
                330                 335                 340

cgt tgg tct tat acg gaa ttg gaa tac tac a gc aca acc aat gat gac     1232
Arg Trp Ser Tyr Thr Glu Leu Glu Tyr Tyr S er Thr Thr Asn Asp Asp
            345                 350                 355

cct tta gga ggt aac agt gct gcc act cga g tt gtt cgc ggc ggc gat     1280
Pro Leu Gly Gly Asn Ser Ala Ala Thr Arg V al Val Arg Gly Gly Asp
        360                 365                 370

ttg gaa aat ttt gca tat tca aga gta tac c ca tca ttg tca cag cag     1328
Leu Glu Asn Phe Ala Tyr Ser Arg Val Tyr P ro Ser Leu Ser Gln Gln
    375                 380                 385

caa caa ttg caa gag cat ccg caa caa caa c aa caa tca ctg tct aat     1376
Gln Gln Leu Gln Glu His Pro Gln Gln Gln G ln Gln Ser Ser Ser Asn
390                 395                 400                 405

caa gaa aac ata caa gag gag gtg ttt gaa a tg ggc acc atc tca cgt     1424
Gln Glu Asn Ile Gln Glu Glu Val Phe Glu M et Gly Thr Ile Ser Arg
                410                 415                 420

tca aga tca tca cca agg tcc ttt gtt tct c tt gga agt agc acc aat     1472
Ser Arg Ser Ser Pro Arg Ser Phe Val Ser L eu Gly Ser Ser Thr Asn
            425                 430                 435

gtt gct gaa gag aac ttt gac ctt gct gat g ag gaa gaa gat atc ggt     1520
Val Ala Glu Glu Asn Phe Asp Leu Ala Asp G lu Glu Glu Asp Ile Gly
        440                 445                 450

tca gga tca tca aaa act ccc tca gta ttt g aa gaa gat aca caa aat     1568
Ser Gly Ser Ser Lys Thr Pro Ser Val Phe G lu Glu Asp Thr Gln Asn
    455                 460                 465

tac gtc gtt tct caa act acc tcc gtt gaa g ac ttg act aat aat aca     1616
Tyr Val Val Ser Gln Thr Thr Ser Val Glu A sp Leu Thr Asn Asn Thr
470                 475                 480                 485

caa gca tca gct gca ggc aac gga gct acc g at aag tca tca aga ctt     1664
Gln Ala Ser Ala Ala Gly Asn Gly Ala Thr A sp Lys Ser Ser Arg Leu
                490                 495                 500

gga atc aat ggt tga acaaagggta gatgtattag aagagtaa tc gtttcttttt     1719
Gly Ile Asn Gly
            505
```

-continued

```
taatggctgc atttgtctag aagagttcga ttataacgat gtttgatgat g tttatgttg   1779

atgattcacg atttttacga attgtacaag aaccctattc acaacctgag a tgggattag   1839

aatgtattga acttggaaaa gatatgggac gtgtgcttgg aatgtcctcc t tttctcata   1899

tccactgccc cattgctatc cctttacaag attattacca tgttatgtct              1949


<210> SEQ ID NO 8
<211> LENGTH: 505
<212> TYPE: PRT
<213> ORGANISM: Candida parapsilosis

<400> SEQUENCE: 8

Met Ser Arg Thr Tyr Asn Gly Ser Ser Ser S er Ser Ile Phe Ser Lys
  1               5                  10                  15

Pro Arg Arg Phe Phe Asn Asn Tyr Phe Leu S er Glu Lys Ser Pro Thr
             20                  25                  30

Ser Thr Leu Pro Asp Leu Glu Thr Asn Thr S er Ile Arg Thr Ser Leu
         35                  40                  45

His Arg Leu Arg His His Lys Phe Ile Lys G ly Glu Ile Leu His Tyr
     50                  55                  60

Gly Phe Leu Ser Phe Val Trp Leu Phe Val P he Thr Ile Tyr Pro Ala
 65                  70                  75                  80

Ser Ile Leu Phe Lys Ile Pro Val Leu Leu A la Leu Leu Thr Ile Ile
                 85                  90                  95

Thr Ile Pro Ala Thr Ser Gln Phe Phe Leu P ro Ala Leu Pro Ile Leu
            100                 105                 110

Thr Trp Leu Gly Phe Tyr Phe Thr Ser Ser L ys Ile Pro His Ser Trp
        115                 120                 125

Lys Pro Ala Ile Ser Val Lys Val Leu Pro A la Met Glu Thr Ile Leu
    130                 135                 140

Tyr Gly Asp Asp Leu Ser Asn Val Leu Ala T hr Ile Thr Asn Arg Gly
145                 150                 155                 160

Leu Asp Ile Leu Gly Trp Leu Pro Tyr Gly L eu Phe His Phe Gly Ala
                165                 170                 175

Pro Phe Val Val Ala Ala Ile Met Phe Phe P he Ala Pro Pro Thr Ser
            180                 185                 190

Leu Arg Ser Phe Ala Phe Ala Phe Gly Tyr M et Asn Leu Phe Gly Val
        195                 200                 205

Ile Ile Gln Met Met Phe Pro Ala Ala Pro P ro Trp Tyr Lys Asn Leu
    210                 215                 220

Tyr Gly Leu Gln Pro Ala Asn Tyr Thr Met H is Gly Ser Pro Gly Gly
225                 230                 235                 240

Leu Gly Arg Ile Asp Glu Leu Leu Gly Val A sp Met Tyr Thr Thr Gly
                245                 250                 255

Phe Ser Asn Ser Pro Val Ile Phe Gly Ala P he Pro Ser Leu His Ser
            260                 265                 270

Gly Cys Cys Ile Met Glu Val Leu Phe Met C ys Trp Leu Phe Pro Arg
        275                 280                 285

Leu Lys Val Leu Trp Val Phe Tyr Ala Ser T rp Leu Trp Trp Ser Thr
    290                 295                 300

Met Tyr Leu Thr His His Tyr Phe Val Asp L eu Thr Gly Gly Ala Val
305                 310                 315                 320

Leu Ser Leu Val Val Phe Glu Phe Val Lys P he Lys Tyr Leu Pro Lys
                325                 330                 335
```

-continued

```
Ala Asn Lys Arg Cys Arg Trp Ser Tyr Thr G lu Leu Glu Tyr Tyr Ser
            340                 345                 350

Thr Thr Asn Asp Asp Pro Leu Gly Gly Asn S er Ala Ala Thr Arg Val
        355                 360                 365

Val Arg Gly Gly Asp Leu Glu Asn Phe Ala T yr Ser Arg Val Tyr Pro
    370                 375                 380

Ser Leu Ser Gln Gln Gln Gln Leu Gln Glu H is Pro Gln Gln Gln Gln
385                 390                 395                 400

Gln Ser Ser Ser Asn Gln Glu Asn Ile Gln G lu Glu Val Phe Glu Met
                405                 410                 415

Gly Thr Ile Ser Arg Ser Arg Ser Ser Pro A rg Ser Phe Val Ser Leu
            420                 425                 430

Gly Ser Ser Thr Asn Val Ala Glu Glu Asn P he Asp Leu Ala Asp Glu
        435                 440                 445

Glu Glu Asp Ile Gly Ser Gly Ser Ser Lys T hr Pro Ser Val Phe Glu
    450                 455                 460

Glu Asp Thr Gln Asn Tyr Val Val Ser Gln T hr Thr Ser Val Glu Asp
465                 470                 475                 480

Leu Thr Asn Asn Thr Gln Ala Ser Ala Ala G ly Asn Gly Ala Thr Asp
                485                 490                 495

Lys Ser Ser Arg Leu Gly Ile Asn Gly
            500                 505


<210> SEQ ID NO 9
<211> LENGTH: 1788
<212> TYPE: RNA
<213> ORGANISM: Candida parapsilosis

<400> SEQUENCE: 9

augucacgca cuuacaaugg gucuuccucc ucaucaauau uucugaaacc a cgucgauuu     60

uucaauaacu acuuucuacu ggaaaaauca ccaacuucaa cauuaccuga u uuagaaaca    120

aacacuagca ucagaacuag ucuucauaga cuaagacauc acaaauucau a aagggagag    180

auuuuacacu augguuucu uucuuuguu ugguuauuug ucuuuaccau a uacccagca    240

uccaucuugu uuaaaauucc aguuuuacuu gcauugcuaa ccauuauuac u auuccagca    300

acuucacaau uuuuuuuacc agcacuuccc auuuugacuu gguuggguuu u uacuucacu    360

aguuccaaaa uaccucauuc uuggaaacca gcuauuucag ucaagguuuu a ccagccaug    420

gagacuaucu uguaugguga ugauuuauca aauguauugg caaccaucac u aaccguggu    480

uuggauauuu ugggcugguu accuuauggu uuauuucauu uuggugcucc a uuuguugua    540

gcugcaauua uguuuuucuu ugcuccacca acuaguuuaa gaucauuugc g uuugcuuuu    600

gguuauauga acuuguuugg gguuauuauu caaaugaugu uuccagcugc u ccaccuugg    660

uacaagaauu uguauggauu acaaccagcc aacuauacca ugcauggcuc a ccaggugga    720

uugggccgua uagaugaauu auugggaguc gauauguaca ccacuggguu c uccaacuca    780

ccgguuauuu uuggugcuuu cccaucauua cauucagguu guuguauuau g gagguuuug    840

uuuauguguu gguuauuucc ccguuugaaa guacuuuggg uguuuuaugc a ucuugguua    900

ugguggagua caauguacuu gacucaucac uauuuuguug auuuaacugg u ggugcugua    960

uuaucauugg uuguuuuuga auuugucaag uuuaaauacc uaccuaaggc u aacaagcgu   1020

ugucguuggu cuuauacgga auuggaauac uacagcacaa ccaaugauga c ccuuuagga   1080

gguaacagug cugccacucg aguuguucgc ggcggcgauu uggaaaauuu u gcauauuca   1140
```

-continued

```
agaguauacc caucauuguc acagcagcaa caauugcaag agcauccgca a caacaacaa   1200

caaucacugu cuaaucaaga aaacauacaa gaggaggugu uugaaauggg c accaucuca   1260

cguucaagau caucaccaag guccuuuguu ucucuuggaa guagcaccaa u guugcugaa   1320

gagaacuuug accuugcuga ugaggaagaa gauaucgguu caggaucauc a aaaacuccc   1380

ucaguauuug aagaagauac acaaaauuac gucguuucuc aaacuaccuc c guugaagac   1440

uugacuaaua auacacaagc aucagcugca ggcaacggag cuaccgauaa g ucaucaaga   1500

cuuggaauca augguugaac aaaggguaga uguauuagaa gaguaaucgu u ucuuuuuua   1560

auggcugcau uugucuagaa gaguucgauu auaacgaugu uugaugaugu u uauguugau   1620

gauucacgau uuuuacgaau uguacaagaa cccuauucac aaccugagau g ggauuagaa   1680

uguauugaac uuggaaaaga uaugggacgu gugcuuggaa uguccuccuu u ucucauauc   1740

cacugcccca uugcuauccc uuuacaagau uauuaccaug uuaugucu                1788
```

<210> SEQ ID NO 10
<211> LENGTH: 2214
<212> TYPE: DNA
<213> ORGANISM: Candida tropicalis
<220> FEATURE:
<221> NAME/KEY: CDS
<222> LOCATION: (601)..(1974)

<400> SEQUENCE: 10

```
cgatggtgat ttctttttct ctcctattcc tgtaccccgc aaatgtgtga t ttcaatccc     60

aaggtgccaa agcacactga tgttggcttg aaagactcag atatggagct t tgtaatata    120

agaaaaatgc caaagtgctt ttcttgccaa tcattgtcga tttggacttt t ctgcctctg    180

tctcactttg catctttagt gacgcatacg ggaaaaaatg taaaatgcgc t gaccataaa    240

tgacattcgg aacataatgc atagaatatt aataccgcat accgataaca g aagtcacaa    300

acgtcacaaa acgtttcaaa aaaacagaaa caggcaagcc tgaaagttga a cacagccac    360

ttcttcccca aactatgaaa acttggtcgt tgcaagatca ttcacttgcg c ccctatttt    420

atagcatgga aaggatgcgt ttctgttccg gcccatttgc gcgcatttga g gtcacgtgc    480

gctgcatcgt cacggcccat tccttttct atccttttat tttatgttgc t tcagcccca    540

acgctgaaag gccgtctttt ccagcagaat ccattactct gctatatttc c ctcattcca    600

atg tca acg gtc cta agg ttc aag cct ttc c gc gtt gct tac aag caa      648
Met Ser Thr Val Leu Arg Phe Lys Pro Phe A rg Val Ala Tyr Lys Gln
  1               5                  10                  15

ttc cac aat tat ttt ttg ctg gag aaa gaa g ca gga tgc act ttg gcg      696
Phe His Asn Tyr Phe Leu Leu Glu Lys Glu A la Gly Cys Thr Leu Ala
             20                  25                  30

gat ctt gat ttc gat act gat atc cgc aag t cc atc cag aaa cta cgt      744
Asp Leu Asp Phe Asp Thr Asp Ile Arg Lys S er Ile Gln Lys Leu Arg
         35                  40                  45

tcc cat gag ttt acg ccg ggc gaa ata gtg c ac tac act ttc ctc acg      792
Ser His Glu Phe Thr Pro Gly Glu Ile Val H is Tyr Thr Phe Leu Thr
     50                  55                  60

ctg ttg atc ttg ttt gtt tat gtc att ttc c cc gcg tcg ttt ttg ctc      840
Ser Leu Ile Leu Phe Val Tyr Val Ile Phe P ro Ala Ser Phe Leu Leu
 65                  70                  75                  80

aaa acg ccc atc ttg gcg gct ttc ggc ttt t gt ttc tta ttg ccc ttg      888
Lys Thr Pro Ile Leu Ala Ala Phe Gly Phe C ys Phe Leu Leu Pro Leu
                 85                  90                  95

acg tcc cag ttt ttc gtg tca gcg ttg ccc a tt ttc aca tgg ttg gcg      936
```

-continued

```
Thr Ser Gln Phe Phe Val Ser Ala Leu Pro I le Phe Thr Trp Leu Ala
            100                 105                 110

ctt ttc ttc tct gcc agc aag atc cct gtg g ac tgg aag cct gtc att      984
Leu Phe Phe Ser Ala Ser Lys Ile Pro Val A sp Trp Lys Pro Val Ile
        115                 120                 125

agc gtc aag ttt ctt cct gcc atg gaa act a tc ttg tac gga gac aac     1032
Ser Val Lys Phe Leu Pro Ala Met Glu Thr I le Leu Tyr Gly Asp Asn
    130                 135                 140

ttg tcg aat gtt ttg gca gcc acc aac aac t gg gtg cta gat atc ttg     1080
Leu Ser Asn Val Leu Ala Ala Thr Asn Asn T rp Val Leu Asp Ile Leu
145                 150                 155                 160

gcg tgg ttg ccc tac ggt atc atc cac ttt c tg tct cca ttt gta gtt     1128
Ala Trp Leu Pro Tyr Gly Ile Ile His Phe S er Ser Pro Phe Val Val
                165                 170                 175

gcg ctc ttc att ttc ctt ttt gct ccg ccc a ct tct ttg cgc tcg ttt     1176
Ala Leu Phe Ile Phe Leu Phe Ala Pro Pro T hr Ser Leu Arg Ser Phe
            180                 185                 190

ggc ttc gcc ttt ggc tac atg aat gtg gtt g gt gtg ttg atc cag ctt     1224
Gly Phe Ala Phe Gly Tyr Met Asn Val Val G ly Val Leu Ile Gln Leu
        195                 200                 205

tgt ttc ccc tca gct gct ccg tgg tac aag a ac ttg cac ggc cta gaa     1272
Cys Phe Pro Ser Ala Ala Pro Trp Tyr Lys A sn Leu His Gly Leu Glu
    210                 215                 220

cct gca aat tat tcc atg aac ggg tct cct g gt ggc ttg ggc cgc att     1320
Pro Ala Asn Tyr Ser Met Asn Gly Ser Pro G ly Gly Leu Gly Arg Ile
225                 230                 235                 240

gac gag ctt ttc ggt gtc gac atg tac acc a ct act ttc atg aac tca     1368
Asp Glu Leu Phe Gly Val Asp Met Tyr Thr T hr Thr Phe Met Asn Ser
                245                 250                 255

cca ttg gtt ttc ggc gcg ttc ccc tcg ctc c at tcg ggc tgc gca gtc     1416
Pro Leu Val Phe Gly Ala Phe Pro Ser Leu H is Ser Gly Cys Ala Val
            260                 265                 270

atg gat gtg ctc ttt ttg tgc tgg ctc ttc c ct cgt ttc acc tat gtt     1464
Met Asp Val Leu Phe Leu Cys Trp Leu Phe P ro Arg Phe Thr Tyr Val
        275                 280                 285

tgg tgg agc tac gcc tgt ctt ttg tgg tgg a gc acc atg tat ttg acg     1512
Trp Trp Ser Tyr Ala Cys Leu Leu Trp Trp S er Thr Met Tyr Leu Thr
    290                 295                 300

cac cac tat ttt atc gac ttg atc ttc ggt g cc gct ttg tct gtg cta     1560
His His Tyr Phe Ile Asp Leu Ile Phe Gly A la Ala Leu Ser Val Leu
305                 310                 315                 320

gtt ttc aac tat gtc aag tac acg cag ttg c ca gtg gtg gac ccc acc     1608
Val Phe Asn Tyr Val Lys Tyr Thr Gln Leu P ro Val Val Asp Pro Thr
                325                 330                 335

aag ttc tgt cgc tgg ctg tac acc acc gtg g ag ctt ctt gac att aac     1656
Lys Phe Cys Arg Trp Ser Tyr Thr Thr Val G lu Leu Leu Asp Ile Asn
            340                 345                 350

gcc aac gac cca ttg cag agt ttc gtg cca t ta cac gga gac atg gag     1704
Ala Asn Asp Pro Leu Gln Ser Phe Val Pro L eu His Gly Asp Met Glu
        355                 360                 365

gaa ggt atg ctg cat ccc ttt tac cac gcg c ca gcg ctt gag aat ttc     1752
Glu Gly Met Ser His Pro Phe Tyr His Ala P ro Ala Leu Glu Asn Phe
    370                 375                 380

gaa atg tct act ata aac cgt tca cgg gaa a gc gtg gct gcg ccg ttt     1800
Glu Met Ser Thr Ile Asn Arg Ser Arg Glu S er Val Ala Ala Pro Phe
385                 390                 395                 400

ccg acc ata gcc gag gat gtg gct gag gaa a cc gac agc agc gcg tcc     1848
Pro Thr Ile Ala Glu Asp Val Ala Glu Glu T hr Asp Ser Ser Ala Ser
                405                 410                 415
```

-continued

```
aat tcg gtt ttt gat gct gag cgt ttt gac g aa gaa acg cat cct agc     1896
Asn Ser Val Phe Asp Ala Glu Arg Phe Asp G lu Glu Thr His Pro Ser
            420                 425                 430

ctg cgt acg tcc agc acc tcg ttg aac gac t tg ctt ctt ccc ctg agc     1944
Ser Arg Thr Ser Ser Thr Ser Leu Asn Asp L eu Leu Leu Pro Ser Ser
        435                 440                 445

tcg agc agc tca aag ccc aaa aga agc acg t agcctttta cattgtcgca       1994
Ser Ser Ser Ser Lys Pro Lys Arg Ser Thr
    450                 455

ccgctctttg gccaggagca ctttaatatt ggccgtgtat actacataaa t gcgacgtct   2054

atcgtgatgc tatgtacatt gtgagtccta gctcggtata tgatatatcc t ctttcgttt   2114

tcgttcgtag cttccttcac ttcctaatcg ttccttctcc ttagtttgac a ccttctcga   2174

acactctttg gtaagtagtg cccacattca agttgccctt                         2214


<210> SEQ ID NO 11
<211> LENGTH: 458
<212> TYPE: PRT
<213> ORGANISM: Candida tropicalis

<400> SEQUENCE: 11

Met Ser Thr Val Leu Arg Phe Lys Pro Phe A rg Val Ala Tyr Lys Gln
  1               5                  10                  15

Phe His Asn Tyr Phe Leu Ser Glu Lys Glu A la Gly Cys Thr Leu Ala
             20                  25                  30

Asp Leu Asp Phe Asp Thr Asp Ile Arg Lys S er Ile Gln Lys Leu Arg
         35                  40                  45

Ser His Glu Phe Thr Pro Gly Glu Ile Val H is Tyr Thr Phe Leu Thr
     50                  55                  60

Leu Ser Ile Leu Phe Val Tyr Val Ile Phe P ro Ala Ser Phe Leu Leu
 65                  70                  75                  80

Lys Thr Pro Ile Leu Ala Ala Phe Gly Phe C ys Phe Leu Leu Pro Leu
                 85                  90                  95

Thr Ser Gln Phe Phe Val Ser Ala Leu Pro I le Phe Thr Trp Leu Ala
            100                 105                 110

Leu Phe Phe Ser Ala Ser Lys Ile Pro Val A sp Trp Lys Pro Val Ile
        115                 120                 125

Ser Val Lys Phe Leu Pro Ala Met Glu Thr I le Leu Tyr Gly Asp Asn
    130                 135                 140

Leu Ser Asn Val Leu Ala Ala Thr Asn Asn T rp Val Leu Asp Ile Leu
145                 150                 155                 160

Ala Trp Leu Pro Tyr Gly Ile Ile His Phe S er Ser Pro Phe Val Val
                165                 170                 175

Ala Leu Phe Ile Phe Leu Phe Ala Pro Pro T hr Ser Leu Arg Ser Phe
            180                 185                 190

Gly Phe Ala Phe Gly Tyr Met Asn Val Val G ly Val Leu Ile Gln Leu
        195                 200                 205

Cys Phe Pro Ser Ala Ala Pro Trp Tyr Lys A sn Leu His Gly Leu Glu
    210                 215                 220

Pro Ala Asn Tyr Ser Met Asn Gly Ser Pro G ly Gly Leu Gly Arg Ile
225                 230                 235                 240

Asp Glu Leu Phe Gly Val Asp Met Tyr Thr T hr Thr Phe Met Asn Ser
                245                 250                 255

Pro Leu Val Phe Gly Ala Phe Pro Ser Leu H is Ser Gly Cys Ala Val
            260                 265                 270
```

-continued

```
Met Asp Val Leu Phe Leu Cys Trp Leu Phe P ro Arg Phe Thr Tyr Val
        275                 280                 285

Trp Trp Ser Tyr Ala Cys Leu Leu Trp Trp S er Thr Met Tyr Leu Thr
    290                 295                 300

His His Tyr Phe Ile Asp Leu Ile Phe Gly A la Ala Leu Ser Val Leu
305                 310                 315                 320

Val Phe Asn Tyr Val Lys Tyr Thr Gln Leu P ro Val Val Asp Pro Thr
                325                 330                 335

Lys Phe Cys Arg Trp Ser Tyr Thr Thr Val G lu Leu Leu Asp Ile Asn
            340                 345                 350

Ala Asn Asp Pro Leu Gln Ser Phe Val Pro L eu His Gly Asp Met Glu
        355                 360                 365

Glu Gly Met Ser His Pro Phe Tyr His Ala P ro Ala Leu Glu Asn Phe
    370                 375                 380

Glu Met Ser Thr Ile Asn Arg Ser Arg Glu S er Val Ala Ala Pro Phe
385                 390                 395                 400

Pro Thr Ile Ala Glu Asp Val Ala Glu Glu T hr Asp Ser Ser Ala Ser
                405                 410                 415

Asn Ser Val Phe Asp Ala Glu Arg Phe Asp G lu Glu Thr His Pro Ser
            420                 425                 430

Ser Arg Thr Ser Ser Thr Ser Leu Asn Asp L eu Leu Leu Pro Ser Ser
        435                 440                 445

Ser Ser Ser Ser Lys Pro Lys Arg Ser Thr
    450                 455


<210> SEQ ID NO 12
<211> LENGTH: 2214
<212> TYPE: RNA
<213> ORGANISM: Candida tropicalis

<400> SEQUENCE: 12

cgauggugau uucuuuuucu cuccuauucc uguaccccgc aaauguguga u uucaauccc      60

aaggugccaa agcacacuga uguuggcuug aaagacucag auauggagcu u uguaauaua     120

agaaaaaugc caaagugcuu uucuugccaa ucauugucga uuuggacuuu u cugccucug     180

ucucacuuug caucuuuagu gacgcauacg ggaaaaaaug uaaaaugcgc u gaccauaaa     240

ugacauucgg aacauaaugc auagaauauu aauaccgcau accgauaaca g aagucacaa     300

acgucacaaa acguuucaaa aaaacagaaa caggcaagcc ugaaaguuga a cacagccac     360

uucuucccca aacuaugaaa acuuggucgu ugcaagauca uucacuugcg c cccuauuuu     420

auagcaugga aaggaugcgu uucuguuccg gcccauuugc gcgcauuuga g gucacgugc     480

gcugcaucgu cacggcccau uccuuuuucu auccuuuuau uuuauguugc u ucagcccca     540

acgcugaaag gccgucuuuu ccagcagaau ccauuacucu gcuauauuuc c cucauucca     600

augucaacgg uccuaagguu caagccuuuc cgcguugcuu acaagcaauu c cacaauuau     660

uuuuugcugg agaaagaagc aggaugcacu uuggcggauc uugauuucga u acugauauc     720

cgcaagucca uccagaaacu acguucccau gaguuuacgc cgggcgaaau a gugcacuac     780

acuuuccuca cgcuguugau cuuguuuguu uaugucauuu uccccgcguc g uuuuugcuc     840

aaaacgccca ucuuggcggc uuucggcuuu uguuucuuau ugcccuugac g ucccaguuu     900

uucgugucag cguugcccau uuucacaugg uuggcgcuuu ucuucucugc c agcaagauc     960

ccuguggacu ggaagccugu cauuagcguc aaguuucuuc cugccaugga a acuaucuug    1020

uacggagaca acuugucgaa uguuuuggca gccaccaaca acugggugcu a gauaucuug    1080
```

-continued

```
gcgugguugc ccuacgguau cauccacuuu cugucuccau uuguaguugc g cucuucauu   1140

uuccuuuuug cuccgcccac uucuuugcgc ucguuuggcu ucgccuuugg c uacaugaau   1200

gugguuggug uguugaucca gcuuuguuuc cccucagcug cuccguggua c aagaacuug   1260

cacggccuag aaccugcaaa uuauuccaug aacgggucuc cugguggcuu g ggccgcauu   1320

gacgagcuuu ucggugucga cauguacacc acuacuuuca ugaacucacc a uuggguuuuc   1380

ggcgcguucc ccucgcucca uucgggcugc gcagucaugg augugcucuu u uugugcugg   1440

cucuucccuc guuucaccua uguuuggugg agcuacgccu gucuuuugug g uggagcacc   1500

auguauuuga cgcaccacua uuuuaucgac uugaucuucg gugccgcuuu g ucugugcua   1560

guuuucaacu augucaagua cacgcaguug ccaguggugg accccaccaa g uucugucgc   1620

uggcuguaca ccaccgugga gcuucuugac auuaacgcca acgacccauu g cagaguuuc   1680

gugccauuac acggagacau ggaggaaggu augcugcauc ccuuuuacca c gcgccagcg   1740

cuugagaauu ucgaaauguc uacuauaaac cguucacggg aaagcguggc u gcgccguuu   1800

ccgaccauag ccgaggaugu ggcugaggaa accgacagca gcgcguccaa u ucgguuuuu   1860

gaugcugagc guuuugacga agaaacgcau ccuagccugc guacguccag c accucguug   1920

aacgacuugc uucuuccccu gagcucgagc agcucaaagc ccaaaagaag c acguagccu   1980

uuuacauugu cgcaccgcuc uuuggccagg agcacuuuaa uauuggccgu g uauacuaca   2040

uaaaugcgac gucuaucgug augcuaugua cauugugagu ccuagcucgg u auaugauau   2100

auccucuuuc guuuucguuc guagcuuccu ucacuuccua aucguuccuu c uccuuaguu   2160

ugacaccuuc ucgaacacuc uuugguaagu agugcccaca uucaaguugc c cuu         2214
```

<210> SEQ ID NO 13
<211> LENGTH: 2935
<212> TYPE: DNA
<213> ORGANISM: Aspergillus fumigatus
<220> FEATURE:
<221> NAME/KEY: CDS
<222> LOCATION: (450)..(1757)

<400> SEQUENCE: 13

```
attttcttcc ccataacaac tcttctcgcc cttcctccgg ctccgtggcc a aattgtttt     60

atgcagcgcc tcctagcgat ttaacctcgt tctcgttgcc cttgcctgtc c gccttgcgt    120

cagtacgacc cttgcaacgt gaccttcccc agagtatcct cgtttggccg c tggagaccg    180

gagcttgcac cctcataaac tagctcttcg aaatcaattc tccgttctcc a gagattatc    240

ggatcgaatc tctccgctgt cgacaccttt cgtctctcgg tgatcctcgc c cttggagtc    300

tcgtcacgtt gacgccttga acccctggcc gccaactcca cataggagac c acacttcat    360

tcttcccccg ccataattgc agcaccctcc gtctcccttc gagctcctcc t ggatcatca    420

agtccgaaag gattagactc gtcgcagcg atg aat acc acc ct t cca tcc tgg      473
                                Met Asn T hr Thr Leu Pro Ser Trp
                                  1               5

aag gat cgg acg caa aac cag ttc ggc aag c tc cag atc caa gtc cca      521
Lys Asp Arg Thr Gln Asn Gln Phe Gly Lys L eu Gln Ile Gln Val Pro
     10                  15                  20

tgg cgc acc ata caa ctt ctc gtg ccg cac c gt atg cga cgg aag att      569
Trp Arg Thr Ile Gln Leu Leu Val Pro His A rg Met Arg Arg Lys Ile
 25                  30                  35                  40

cgg tcc aag ctg cgc agt cgg atc tcg cct a cc tca tcg ata tcc tcg      617
Arg Ser Lys Leu Arg Ser Arg Ile Ser Pro T hr Ser Ser Ile Ser Ser
                 45                  50                  55
```

-continued

```
ttg cag acg tca ttc tca cct gtc gat aca c tc agg tcg ctg caa agt      665
Leu Gln Thr Ser Phe Ser Pro Val Asp Thr L eu Arg Ser Leu Gln Ser
            60                  65                  70

cat aga tgg acg ctc tat gac ttt cag tat c tt ttg ctg ctg att gtc      713
His Arg Trp Thr Leu Tyr Asp Phe Gln Tyr L eu Leu Leu Leu Ile Val
        75                  80                  85

ggc ata ttc tcg ctg agc gtt atg gaa tca c ct gga cca ttg gca aag      761
Gly Ile Phe Ser Leu Ser Val Met Glu Ser P ro Gly Pro Leu Ala Lys
    90                  95                  100

acc gcc gcg ttt acg cta ctt ctc gtc tct c tc ctt ctc ccg att acg      809
Thr Ala Ala Phe Thr Leu Leu Leu Val Ser L eu Leu Leu Pro Ile Thr
105                 110                 115                 120

cgc cag ttc ttc ttg cca ttc ctc ccg att g ca gga tgg ctt ata ttt      857
Arg Gln Phe Phe Leu Pro Phe Leu Pro Ile A la Gly Trp Leu Ile Phe
                125                 130                 135

ttc tac gct tgc cag ttc atc ccg agc gac t gg cgc cct gca atc tgg      905
Phe Tyr Ala Cys Gln Phe Ile Pro Ser Asp T rp Arg Pro Ala Ile Trp
            140                 145                 150

gtt cgc gtg ctg ccg gct ctg gaa aac att c tc tac ggt gct aat atc      953
Val Arg Val Leu Pro Ala Leu Glu Asn Ile L eu Tyr Gly Ala Asn Ile
        155                 160                 165

agt aac atc ctt tcc gct cac caa aat gtg g tg ctt gac gtt ttg gcg     1001
Ser Asn Ile Leu Ser Ala His Gln Asn Val V al Leu Asp Val Leu Ala
    170                 175                 180

tgg ctt ccc tac gga atc tgc cat tat ggc g cg cca ttt gtg tgc tca     1049
Trp Leu Pro Tyr Gly Ile Cys His Tyr Gly A la Pro Phe Val Cys Ser
185                 190                 195                 200

gcg atc atg ttc atc ttt ggt cct ccc ggc a cc gtc ccc ctt ttc gct     1097
Ala Ile Met Phe Ile Phe Gly Pro Pro Gly T hr Val Pro Leu Phe Ala
                205                 210                 215

cga act ttt gga tac atc agc atg gct gca g tc acc att cag ctg ttt     1145
Arg Thr Phe Gly Tyr Ile Ser Met Ala Ala V al Thr Ile Gln Leu Phe
            220                 225                 230

ttc ccc tgc tct cct ccg tgg tac gaa aat c tg tat ggt ttg gct ccg     1193
Phe Pro Cys Ser Pro Pro Trp Tyr Glu Asn L eu Tyr Gly Leu Ala Pro
        235                 240                 245

gct gat tac tcc atg ccg ggt aat cct gcg g gc ctt gct cgc atc gat     1241
Ala Asp Tyr Ser Met Pro Gly Asn Pro Ala G ly Leu Ala Arg Ile Asp
    250                 255                 260

gag ctt ttt ggg ata gac ttg tac aca tcg g gc ttc aga caa tct ccc     1289
Glu Leu Phe Gly Ile Asp Leu Tyr Thr Ser G ly Phe Arg Gln Ser Pro
265                 270                 275                 280

gtc gtg ttt ggc gca ttt cct tcc cta cat g cc gct gat tcg aca ctt     1337
Val Val Phe Gly Ala Phe Pro Ser Leu His A la Ala Asp Ser Thr Leu
                285                 290                 295

gca gct cta ttt atg agc caa gtg ttc cca c gg ttg aag ccc ttg ttt     1385
Ala Ala Leu Phe Met Ser Gln Val Phe Pro A rg Leu Lys Pro Leu Phe
            300                 305                 310

gtc atc tat act ctc tgg atg tgg tgg gct a ca atg tat ctt tcg cac     1433
Val Ile Tyr Thr Leu Trp Met Trp Trp Ala T hr Met Tyr Leu Ser His
        315                 320                 325

cac tac gct gtt gat ctg gtc ggt ggt ggc c tc ttg gca act gtc gcg     1481
His Tyr Ala Val Asp Leu Val Gly Gly Gly L eu Leu Ala Thr Val Ala
    330                 335                 340

ttc tac ttt gct aaa acg cgg ttc atg cct c gc gtc cag aat gat aag     1529
Phe Tyr Phe Ala Lys Thr Arg Phe Met Pro A rg Val Gln Asn Asp Lys
345                 350                 355                 360

atg ttc cgc tgg gac tac gat tat gtt gag t ca ggc gat tcc gca ctc     1577
Met Phe Arg Trp Asp Tyr Asp Tyr Val Glu S er Gly Asp Ser Ala Leu
```

-continued

```
                365                 370                 375

gac tat ggg tac ggt cca gcc agc ttc gaa g gc gaa ttc aac ctt gat     1625
Asp Tyr Gly Tyr Gly Pro Ala Ser Phe Glu G ly Glu Phe Asn Leu Asp
            380                 385                 390

agc gat gag tgg acc gtt ggt tct tcg tca t cc att tcg tcc ggc tcc     1673
Ser Asp Glu Trp Thr Val Gly Ser Ser Ser S er Ile Ser Ser Gly Ser
        395                 400                 405

ctc agt cca gtt gac gac cac tac tct tgg g ag ggc gag act ctt gcc     1721
Leu Ser Pro Val Asp Asp His Tyr Ser Trp G lu Gly Glu Thr Leu Ala
    410                 415                 420

tct cct gcc acc gag atc gag tct gga agg c at ttc tgatcctgct          1767
Ser Pro Ala Thr Glu Ile Glu Ser Gly Arg H is Phe
425                 430                 435

caatgagcct tgatacgtac tacactgtgt acgtgctact gcattgacta a tgagacggc   1827

gttttcaaac aaattttaac gacatgcttg gttatcgcat tgagctgatt t cgacacata   1887

tatatgttta atacgttttg gggacactcc agggattcat gacggttgct t catatcccg   1947

acctggggat ggattgacct ggttgtgccc aattttcttc tgcctaacgt t ttgattata   2007

catgcatttt tcacgaaacc agccggcccg ccatgatcgt gacctcaatt t gagctcgaa   2067

tcttcctggg gcctccagcg ataattctta atgctcgttc cgagggtgcc a catcggaca   2127

ttcgcttgta caacttttgc agaacgaaca ttttcaccga ttccaacttg a gtcattcgc   2187

ttactacttt caactggtcg agaaacttcg cttcttttca gctcggctag g tgcataaat   2247

attttacatt cgtgtcgatc gctcacattt cacggcgcct ggaaacttgg g ggtttcgat   2307

ttcattggaa aggataaaca acatgggctg ggcgcctttt acacgcacta c attcgctta   2367

gaaaagttct gatgctttta atgattcttg cattggcata tagaaagggg t cctccagac   2427

tcgctactgt ggtcctctct caaccccaca ctcgcttgct tttaacagtg g acaccccgt   2487

ggagctacgt ctccatcaaa tatttggcat caaccggaat cgatgccagg a ggactgagc   2547

ttactcacgg tgaccgtcgg gtaaaaggcg ttctaacaga acatctcctc t atcctcctg   2607

tcccatctcg attctctggc tgctggacgc aacacacctc gctgcacgtt t tcgacttcc   2667

taatacgacc taatatcatt ctcggttttc tttgctctgg ctcgcggccg c catttatat   2727

ggcgtgtcgg ctcgagtctg aagtgaactt ttttctcctt tctggcctcc a caactttcc   2787

gatccctagc agcttcccgt gcacagcgag gtgttgttgg atgattgttc c atagcatta   2847

tcattattcc taatccggta gcgttatgat ttatgaagaa cagtgatgta c attattatg   2907

cggtgactaa aaaaaaaaaa aaaaaaaa                                      2935


<210> SEQ ID NO 14
<211> LENGTH: 436
<212> TYPE: PRT
<213> ORGANISM: Aspergillus fumigatus

<400> SEQUENCE: 14

Met Asn Thr Thr Leu Pro Ser Trp Lys Asp A rg Thr Gln Asn Gln Phe
  1               5                  10                  15

Gly Lys Leu Gln Ile Gln Val Pro Trp Arg T hr Ile Gln Leu Leu Val
            20                  25                  30

Pro His Arg Met Arg Arg Lys Ile Arg Ser L ys Leu Arg Ser Arg Ile
        35                  40                  45

Ser Pro Thr Ser Ser Ile Ser Ser Leu Gln T hr Ser Phe Ser Pro Val
    50                  55                  60

Asp Thr Leu Arg Ser Leu Gln Ser His Arg T rp Thr Leu Tyr Asp Phe
```

-continued

```
 65                  70                  75                  80

Gln Tyr Leu Leu Leu Leu Ile Val Gly Ile P he Ser Leu Ser Val Met
                 85                  90                  95

Glu Ser Pro Gly Pro Leu Ala Lys Thr Ala A la Phe Thr Leu Leu Leu
            100                 105                 110

Val Ser Leu Leu Leu Pro Ile Thr Arg Gln P he Phe Leu Pro Phe Leu
        115                 120                 125

Pro Ile Ala Gly Trp Leu Ile Phe Phe Tyr A la Cys Gln Phe Ile Pro
    130                 135                 140

Ser Asp Trp Arg Pro Ala Ile Trp Val Arg V al Leu Pro Ala Leu Glu
145                 150                 155                 160

Asn Ile Leu Tyr Gly Ala Asn Ile Ser Asn I le Leu Ser Ala His Gln
                165                 170                 175

Asn Val Val Leu Asp Val Leu Ala Trp Leu P ro Tyr Gly Ile Cys His
            180                 185                 190

Tyr Gly Ala Pro Phe Val Cys Ser Ala Ile M et Phe Ile Phe Gly Pro
        195                 200                 205

Pro Gly Thr Val Pro Leu Phe Ala Arg Thr P he Gly Tyr Ile Ser Met
    210                 215                 220

Ala Ala Val Thr Ile Gln Leu Phe Phe Pro C ys Ser Pro Pro Trp Tyr
225                 230                 235                 240

Glu Asn Leu Tyr Gly Leu Ala Pro Ala Asp T yr Ser Met Pro Gly Asn
                245                 250                 255

Pro Ala Gly Leu Ala Arg Ile Asp Glu Leu P he Gly Ile Asp Leu Tyr
            260                 265                 270

Thr Ser Gly Phe Arg Gln Ser Pro Val Val P he Gly Ala Phe Pro Ser
        275                 280                 285

Leu His Ala Ala Asp Ser Thr Leu Ala Ala L eu Phe Met Ser Gln Val
    290                 295                 300

Phe Pro Arg Leu Lys Pro Leu Phe Val Ile T yr Thr Leu Trp Met Trp
305                 310                 315                 320

Trp Ala Thr Met Tyr Leu Ser His His Tyr A la Val Asp Leu Val Gly
                325                 330                 335

Gly Gly Leu Leu Ala Thr Val Ala Phe Tyr P he Ala Lys Thr Arg Phe
            340                 345                 350

Met Pro Arg Val Gln Asn Asp Lys Met Phe A rg Trp Asp Tyr Asp Tyr
        355                 360                 365

Val Glu Ser Gly Asp Ser Ala Leu Asp Tyr G ly Tyr Gly Pro Ala Ser
    370                 375                 380

Phe Glu Gly Glu Phe Asn Leu Asp Ser Asp G lu Trp Thr Val Gly Ser
385                 390                 395                 400

Ser Ser Ser Ile Ser Ser Gly Ser Leu Ser P ro Val Asp Asp His Tyr
                405                 410                 415

Ser Trp Glu Gly Glu Thr Leu Ala Ser Pro A la Thr Glu Ile Glu Ser
            420                 425                 430

Gly Arg His Phe
        435
```

<210> SEQ ID NO 15
<211> LENGTH: 2959
<212> TYPE: RNA
<213> ORGANISM: Aspergillus fumigatus

<400> SEQUENCE: 15

-continued

```
auaugauuua aaauuaaugu uuccauuuuc uuccccauaa caacucuucu c gcccuuccu     60
ccggcuccgu ggccaaauug uuuuaugcag cgccuccuag cgauuuaacc u cguucucgu    120
ugcccuugcc uguccgccuu gcgucaguac gacccuugca acgugaccuu c cccagagua    180
uccucguuug gccgcuggag accggagcuu gcacccucau aaacuagcuc u ucgaaauca    240
auucuccguu cuccagagau uaucggaucg aaucucuccg cugucgacac c uuucgucuc    300
ucggugaucc ucgcccuugg agucucguca cguugacgcc uugaaccccu g gccgccaac    360
uccacauagg agaccacacu ucauucuucc cccgccauaa uugcagcacc c uccgucucc    420
cuucgagcuc cuccuggauc aucaaguccg aaaggauuag acucgucgca g cgaugaaua    480
ccacccuucc auccuggaag gaucggacgc aaaaccaguu cggcaagcuc c agauccaag    540
ucccauggcg caccauacaa cuucucgugc cgcaccguau gcgacggaag a uucggucca    600
agcugcgcag ucggaucucg ccuaccucau cgauauccuc guugcagacg u cauucucac    660
cugucgauac acucaggucg cugcaaaguc auagauggac gcucuaugac u uucaguauc    720
uuuugcugcu gauugucggc auauucucgc ugagcguuau ggaaucaccu g gaccauugg    780
caaagaccgc cgcguuuacg cuacuucucg ucucucuccu ucucccgauu a cgcgccagu    840
ucuucuugcc auuccucccg auugcaggau ggcuuauauu uuucuacgcu u gccaguuca    900
ucccgagcga cuggcgcccu gcaaucuggg uucgcgugcu gccggcucug g aaaacauuc    960
ucuacggugc uaauaucagu aacauccuuu ccgcucacca aaauguggug c uugacguuu   1020
uggcguggcu ucccuacgga aucugccauu auggcgcgcc auuugugugc u cagcgauca   1080
uguucaucuu ugguccuccc ggcaccgucc cccuuuucgc ucgaacuuuu g gauacauca   1140
gcauggcugc agucaccauu cagcuguuuu uccccugcuc uccuccgugg u acgaaaauc   1200
uguaugguuu ggcuccggcu gauuacucca ugccggguaa uccugcgggc c uugcucgca   1260
ucgaugagcu uuuugggaua gacuuguaca caucgggcuu cagacaaucu c ccgucgugu   1320
uuggcgcauu uccuucccua caugccgcug auucgacacu ugcagcucua u uuaugagcc   1380
aaguguuccc acgguugaag cccuuguuug ucaucuauac ucucuggaug u gguggcua   1440
caauguaucu uucgcaccac uacgcuguug aucuggucgg ugguggccuc u uggcaacug   1500
ucgcguucua cuuugcuaaa acgcgguuca ugccucgcgu ccagaaugau a agauguucc   1560
gcugggacua cgauuauguu gagucaggcg auuccgcacu cgacuauggg u acgguccag   1620
ccagcuucga aggcgaauuc aaccuugaua gcgaugagug gaccguuggu u cuucgucau   1680
ccauuucguc cggcucccuc aguccaguug acgaccacua cucuugggag g gcgagacuc   1740
uugccucucc ugccaccgag aucgagucug gaaggcauuu cugauccugc u caaugagcc   1800
uugauacgua cuacacugug uacgugcuac ugcauugacu aaugagacgg c guuuucaaa   1860
caaauuuuaa cgacaugcuu gguuaucgca uugagcugau uucgacacau a uauauguuu   1920
aauacguuuu ggggacacuc cagggauuca ugacgguugc uucauauccc g accuggga   1980
uggauugacc ugguugugcc caauuuucuu cugccuaacg uuuugauuau a caugcauuu   2040
uucacgaaac cagccggccc gccaugaucg ugaccucaau uugagcucga a ucuuccugg   2100
ggccuccagc gauaauucuu aaugcucguu ccgagggugc cacaucggac a uucgcuugu   2160
acaacuuuug cagaacgaac auuuucaccg auuccaacuu gagucauucg c uuacuacuu   2220
ucaacugguc gagaaacuuc gcuucuuuuc agcucggcua ggugcauaaa u auuuuacau   2280
ucgugucgau cgcucacauu ucacggcgcc uggaaacuug gggguuucga u uucauugga   2340
aaggauaaac aacaugggcu gggcgccuuu uacacgcacu acauucgcuu a gaaaaguuc   2400
```

-continued

```
ugaugcuuuu aaugauucuu gcauuggcau auagaaaggg guccuccaga c ucgcuacug   2460

ugguccucuc ucaaccccac acucgcuugc uuuuaacagu ggacaccccg u ggagcuacg   2520

ucuccaucaa auauuuggca ucaaccggaa ucgaugccag gaggacugag c uuacucacg   2580

gugaccgucg gguaaaaggc guucuaacag aacaucuccu cuauccuccu g ucccaucuc   2640

gauucucugg cugcuggacg caacacaccu cgcugcacgu uuucgacuuc c uaauacgac   2700

cuaauaucau ucucgguuuu cuuugcucug gcucgcggcc gccauuuaua u ggcgugucg   2760

gcucgagucu gaagugaacu uuuuucuccu uucuggccuc cacaacuuuc c gaucccuag   2820

cagcuucccg ugcacagcga gguguuguug gaugauuguu ccauagcauu a ucauuauuc   2880

cuaauccggu agcguuauga uuuaugaaga acagugaugu acauuauuau g cggugacua   2940

aaaaaaaaaa aaaaaaaaa                                                2959


<210> SEQ ID NO 16
<211> LENGTH: 2856
<212> TYPE: DNA
<213> ORGANISM: Aspergillus nidulans
<220> FEATURE:
<221> NAME/KEY: CDS
<222> LOCATION: (395)..(1714)

<400> SEQUENCE: 16

ggtttatact ccggctccgt ggccatctgc ctccctcacg acctcctcgt t ccaggtttt     60

cctctcgact gctgcgccct tgcacttcgc cttgcatcag tgaaaccccc t gcaacgtga    120

cggctcaaag acatcctcgt ttggccgctg gagaccggag cgtgcgcttc g tttcgtctt    180

cttcgaaccg atctcaattt ccccgctcgg gttgacgccg tcagcaccct g ctcgttgcc    240

tcccggcttg ttattcaaga cccctttct gccgcttccg cgaccgattt a ttcgtcgcc    300

ttccaactct tgtacaatcg gggggaaaga aagcagacgg agttcgatct g gaggaatta    360

tagctgagtc ttgcccgcaa gactcgccgc aacc atg aat caa aca ctt ccc acg    415
                                      Met Asn Gln Thr Leu Pro Thr
                                        1               5

tgg aag gac cgc acg gac aac cag ttt gga a ag ctt cag atc cag gtt      463
Trp Lys Asp Arg Thr Asp Asn Gln Phe Gly L ys Leu Gln Ile Gln Val
         10                  15                  20

cca tgg cgg tcc atc caa ctg ctc gtc ccg c at cgc atg cgg cgg aag      511
Pro Trp Arg Ser Ile Gln Leu Leu Val Pro H is Arg Met Arg Arg Lys
     25                  30                  35

tta agg tcc aaa ttg cgc agt aga gcg tct c ct acc tcg tca ata gcc      559
Leu Arg Ser Lys Leu Arg Ser Arg Ala Ser P ro Thr Ser Ser Ile Ala
 40                  45                  50                  55

tct tta cag acg tcg tta tcg cct gca gac a ca cta cga tcg ctc caa      607
Ser Leu Gln Thr Ser Leu Ser Pro Ala Asp T hr Leu Arg Ser Leu Gln
                 60                  65                  70

agc cac cga tgg acg gtt tac gac ttc caa t at ctg ctt ctg ttg atc      655
Ser His Arg Trp Thr Val Tyr Asp Phe Gln T yr Leu Leu Leu Leu Ile
             75                  80                  85

gtg ggc atc ttc tct ttg acc gtt atc gag t cg ccc ggg cct ttg ggc      703
Val Gly Ile Phe Ser Leu Thr Val Ile Glu S er Pro Gly Pro Leu Gly
         90                  95                 100

aaa acg gcc att ttc tcc atg ctc cta ttc t ct ctc ctg atc cct atg      751
Lys Thr Ala Ile Phe Ser Met Leu Leu Phe S er Leu Leu Ile Pro Met
    105                 110                 115

acc cgc cag ttc ttc ctc ccg ttt ctg ccg a tt gcc gga tgg ctt ctg      799
Thr Arg Gln Phe Phe Leu Pro Phe Leu Pro I le Ala Gly Trp Leu Leu
120                 125                 130                 135
```

-continued

```
ttt ttc tac gcc tgc cag ttc atc cca agc g at tgg cgc cct gcg att      847
Phe Phe Tyr Ala Cys Gln Phe Ile Pro Ser A sp Trp Arg Pro Ala Ile
                140                 145                 150

tgg gtt cgt gtc ttg cct gca ctg gag aat a tt ctc tac ggc gca aac      895
Trp Val Arg Val Leu Pro Ala Leu Glu Asn I le Leu Tyr Gly Ala Asn
            155                 160                 165

atc agc aac atc cta tcc gct cac cag aac g tt gtg ctt gac gtg ctg      943
Ile Ser Asn Ile Leu Ser Ala His Gln Asn V al Val Leu Asp Val Leu
        170                 175                 180

gcg tgg cta ccc tac ggt atc tgc cac tat g gc gct ccg ttt gtg tgc      991
Ala Trp Leu Pro Tyr Gly Ile Cys His Tyr G ly Ala Pro Phe Val Cys
    185                 190                 195

tcg ttg atc atg ttc atc ttc ggt ccg ccc g gc act gtt ccc ctt ttc     1039
Ser Leu Ile Met Phe Ile Phe Gly Pro Pro G ly Thr Val Pro Leu Phe
200                 205                 210                 215

gcg cgc act ttc ggc tat atc agt atg act g cg gtt act att cag ctg     1087
Ala Arg Thr Phe Gly Tyr Ile Ser Met Thr A la Val Thr Ile Gln Leu
                220                 225                 230

ttt ttc cct tgc tct cca cct tgg tat gag a at cgc tat ggt cta gct     1135
Phe Phe Pro Cys Ser Pro Pro Trp Tyr Glu A sn Arg Tyr Gly Leu Ala
            235                 240                 245

ccg gca gac tac tcc atc caa ggt gat ccc g ca ggg ctt gcc cgc att     1183
Pro Ala Asp Tyr Ser Ile Gln Gly Asp Pro A la Gly Leu Ala Arg Ile
        250                 255                 260

gac aag ctt ttc ggc atc gac ctt tac acg t ct gtt ttc cat cag tcg     1231
Asp Lys Leu Phe Gly Ile Asp Leu Tyr Thr S er Val Phe His Gln Ser
    265                 270                 275

cct gtt gtg ttc ggc gct ttt ccg tcg ctg c at gct gcc gac tca acc     1279
Pro Val Val Phe Gly Ala Phe Pro Ser Leu H is Ala Ala Asp Ser Thr
280                 285                 290                 295

ctg gcc gca ctt ttc atg agt cat gtt ttc c cc cgc atg aag ccc gtc     1327
Leu Ala Ala Leu Phe Met Ser His Val Phe P ro Arg Met Lys Pro Val
                300                 305                 310

ttc gtg acc tat act cta tgg atg tgg tgg g ca aca atg tac ctc tca     1375
Phe Val Thr Tyr Thr Leu Trp Met Trp Trp A la Thr Met Tyr Leu Ser
            315                 320                 325

cat cac tat gcg gtc gat ttg gtt gcg ggt g gt ctc ctg gcc gcc att     1423
His His Tyr Ala Val Asp Leu Val Ala Gly G ly Leu Leu Ala Ala Ile
        330                 335                 340

gct ttc tac ttc gcc aag acc cga ttc ctt c cc cgt gtc cag ctc gac     1471
Ala Phe Tyr Phe Ala Lys Thr Arg Phe Leu P ro Arg Val Gln Leu Asp
    345                 350                 355

aag acc ttc cgt tgg gac tac gac tat gtg g aa ttc ggc gag tct gcc     1519
Lys Thr Phe Arg Trp Asp Tyr Asp Tyr Val G lu Phe Gly Glu Ser Ala
360                 365                 370                 375

ctg gag tat ggg tat ggt gca gct ggc tat g at gga gac ttc aat ctc     1567
Leu Glu Tyr Gly Tyr Gly Ala Ala Gly Tyr A sp Gly Asp Phe Asn Leu
                380                 385                 390

gac agc gat gaa tgg act gtt ggt tct tca t cc tcc gtc tcc tca ggc     1615
Asp Ser Asp Glu Trp Thr Val Gly Ser Ser S er Ser Val Ser Ser Gly
            395                 400                 405

tcc ttg agt ccc gtt gac gat cat tac tca t gg gaa acc gag gca ctg     1663
Ser Leu Ser Pro Val Asp Asp His Tyr Ser T rp Glu Thr Glu Ala Leu
        410                 415                 420

acc tcc cca cat act gat att gag tcc ggc a gg cat act ttc agc cct     1711
Thr Ser Pro His Thr Asp Ile Glu Ser Gly A rg His Thr Phe Ser Pro
    425                 430                 435

tga gtagccacaa accaaactcg atacctgcat atagcgatct cgctcctc ct          1764
```

-continued

```
ccactgcatc tatttacgag acggcgttag aacatttcac gacattctgg c tttattgca   1824

tcgagcacat ttcgacacat atatctttaa tacccttct tcggtgtccc a gatcatcgg   1884

ttcgacctta atgtacctcg gtccgaatcc gcctgggata ctgtttctct t tccgccgca   1944

cttcactgta cattgcttga cattgcgaaa ccgggttggg ctcgaacgtg g gatgggtta   2004

tcgctcatcg ctacacgccg ttgctccatc ataatgttaa tggacacaat g gggctacgc   2064

atcctggtgt ttagtcctgg aagaccatcc gataaccccc gtcggtaaca c tcgcttgtc   2124

tcgtgtccac ccagacacta cttcaattct cacttctatc gtccgctatt a ccttgacct   2184

ggtcgaaccc atccttatta ttcgtttcga ctatgctata tatttatttt t accattcgt   2244

gtcgatcgct catactcttg gcgcttggga ctggaagcat ttatattgga a aaaatcacg   2304

gaatggggcg ccttttcttc ttgcacttca ctcgctgtgc atagacggtt t tacatttct   2364

gctttgcaat gcatcacgaa ctctgcatta gcatatagaa agaggggaag g atggacctt   2424

cttcttgatt gctcgcatgg tttatccatt cgctcaaagt ggattacgtc c acatcttac   2484

ccgggggcta tacacatggc tactgtgttg ctttctgaca ttcgccggac g tgcaaggtt   2544

gggaggagag tctgacgctg acggggcttg ttgaaggatg ttcacgcgtc c cgatttgac   2604

ccggcttcga ctaacctcag attctcgact tgttggacgg tgacttgact t gcttgctat   2664

ggtctgacgc tctcacacct acctatcaca tcctcctcac ctcacaaatt c cgctcatgg   2724

acactatcct cttcttttcg tttcccttgg atagtgtgtg tgtgtgtgtg g ttggggcaa   2784

attatccata gcagcagtat tattagttat aatccggtag tgttatgatt t atgaaggca   2844

acttgtatac ta                                                       2856
```

<210> SEQ ID NO 17
<211> LENGTH: 439
<212> TYPE: PRT
<213> ORGANISM: Aspergillus nidulans

<400> SEQUENCE: 17

```
Met Asn Gln Thr Leu Pro Thr Trp Lys Asp A rg Thr Asp Asn Gln Phe
  1               5                  10                  15

Gly Lys Leu Gln Ile Gln Val Pro Trp Arg S er Ile Gln Leu Leu Val
             20                  25                  30

Pro His Arg Met Arg Arg Lys Leu Arg Ser L ys Leu Arg Ser Arg Ala
         35                  40                  45

Ser Pro Thr Ser Ser Ile Ala Ser Leu Gln T hr Ser Leu Ser Pro Ala
     50                  55                  60

Asp Thr Leu Arg Ser Leu Gln Ser His Arg T rp Thr Val Tyr Asp Phe
 65                  70                  75                  80

Gln Tyr Leu Leu Leu Leu Ile Val Gly Ile P he Ser Leu Thr Val Ile
                 85                  90                  95

Glu Ser Pro Gly Pro Leu Gly Lys Thr Ala I le Phe Ser Met Leu Leu
            100                 105                 110

Phe Ser Leu Leu Ile Pro Met Thr Arg Gln P he Phe Leu Pro Phe Leu
        115                 120                 125

Pro Ile Ala Gly Trp Leu Leu Phe Phe Tyr A la Cys Gln Phe Ile Pro
    130                 135                 140

Ser Asp Trp Arg Pro Ala Ile Trp Val Arg V al Leu Pro Ala Leu Glu
145                 150                 155                 160

Asn Ile Leu Tyr Gly Ala Asn Ile Ser Asn I le Leu Ser Ala His Gln
                165                 170                 175
```

-continued

```
Asn Val Val Leu Asp Val Leu Ala Trp Leu P ro Tyr Gly Ile Cys His
            180                 185                 190

Tyr Gly Ala Pro Phe Val Cys Ser Leu Ile M et Phe Ile Phe Gly Pro
        195                 200                 205

Pro Gly Thr Val Pro Leu Phe Ala Arg Thr P he Gly Tyr Ile Ser Met
    210                 215                 220

Thr Ala Val Thr Ile Gln Leu Phe Phe Pro C ys Ser Pro Pro Trp Tyr
225                 230                 235                 240

Glu Asn Arg Tyr Gly Leu Ala Pro Ala Asp T yr Ser Ile Gln Gly Asp
                245                 250                 255

Pro Ala Gly Leu Ala Arg Ile Asp Lys Leu P he Gly Ile Asp Leu Tyr
            260                 265                 270

Thr Ser Val Phe His Gln Ser Pro Val Val P he Gly Ala Phe Pro Ser
        275                 280                 285

Leu His Ala Ala Asp Ser Thr Leu Ala Ala L eu Phe Met Ser His Val
    290                 295                 300

Phe Pro Arg Met Lys Pro Val Phe Val Thr T yr Thr Leu Trp Met Trp
305                 310                 315                 320

Trp Ala Thr Met Tyr Leu Ser His His Tyr A la Val Asp Leu Val Ala
                325                 330                 335

Gly Gly Leu Leu Ala Ala Ile Ala Phe Tyr P he Ala Lys Thr Arg Phe
            340                 345                 350

Leu Pro Arg Val Gln Leu Asp Lys Thr Phe A rg Trp Asp Tyr Asp Tyr
        355                 360                 365

Val Glu Phe Gly Glu Ser Ala Leu Glu Tyr G ly Tyr Gly Ala Ala Gly
    370                 375                 380

Tyr Asp Gly Asp Phe Asn Leu Asp Ser Asp G lu Trp Thr Val Gly Ser
385                 390                 395                 400

Ser Ser Ser Val Ser Ser Gly Ser Leu Ser P ro Val Asp Asp His Tyr
                405                 410                 415

Ser Trp Glu Thr Glu Ala Leu Thr Ser Pro H is Thr Asp Ile Glu Ser
            420                 425                 430

Gly Arg His Thr Phe Ser Pro
        435
```

<210> SEQ ID NO 18
<211> LENGTH: 2877
<212> TYPE: RNA
<213> ORGANISM: Aspergillus nidulans

<400> SEQUENCE: 18

```
uaaaauuuca uaaauguuuc cgguuuauac uccggcuccg uggccaucug c cucccucac      60

gaccuccucg uuccagguuu uccucucgac ugcugcgccc uugcacuucg c cuugcauca     120

gugaaacccc cugcaacgug acggcucaaa gacauccucg uuuggccgcu g gagaccgga     180

gcgugcgcuu cguuucgucu ucuucgaacc gaucucaauu uccccgcucg g guugacgcc     240

gucagcaccc ugcucguugc cucccggcuu guuauucaag accccuuuuc u gccgcuucc     300

gcgaccgauu uauucgucgc cuuccaacuc uuguacaauc ggggggaaag a aagcagacg     360

gaguucgauc uggaggaauu auagcugagu cuugcccgca agacucgccg c aaccaugaa     420

ucaaacacuu cccacgugga aggaccgcac ggacaaccag uuuggaaagc u ucagaucca     480

gguuccaugg cgguccaucc aacugcucgu cccgcaucgc augcggcgga a guuaagguc     540

caaauugcgc aguagagcgu cuccuaccuc gucaauagcc ucuuuacaga c gucguuauc     600
```

-continued

```
gccugcagac acacuacgau cgcuccaaag ccaccgaugg acgguuuacg a cuuccaaua    660
ucugcuucug uugaucgugg gcaucuucuc uuugaccguu aucgagucgc c cgggccuuu    720
gggcaaaacg gccauuuucu ccaugcuccu auucucucuc cugaucccua u gacccgcca    780
guucuuccuc ccguuucugc cgauugccgg auggcuucug uuuuucuacg c cugccaguu    840
caucccaagc gauuggcgcc cugcgauuug gguucguguc uugccugcac u ggagaauau    900
ucucuacggc gcaaacauca gcaacauccu auccgcucac cagaacguug u gcuugacgu    960
gcuggcgugg cuacccuacg guaucugcca cuauggcgcu ccguuugugu g cucguugau   1020
cauguucauc uucgguccgc ccggcacugu uccccuuuuc gcgcgcacuu u cggcuauau   1080
caguaugacu gcgguuacua uucagcuguu uuucccuugc ucuccaccuu g guaugagaa   1140
ucgcuauggu cuagcuccgg cagacuacuc cauccaaggu gaucccgcag g gcuugcccg   1200
cauugacaag cuuuucggca ucgaccuuua cacgucuguu uuccaucagu c gccuguugu   1260
guucggcgcu uuuccgucgc ugcaugcugc cgacucaacc cuggccgcac u uuucaugag   1320
ucauguuuuc ccccgcauga agcccgucuu cgugaccuau acucuaugga u gugugggc   1380
aacaauguac cucucacauc acuaugcggu cgauuugguu gcgggugguc u ccuggccgc   1440
cauugcuuuc uacuucgcca agacccgauu ccuuccccgu guccagcucg a caagaccuu   1500
ccguugggac uacgacuaug uggaauucgg cgagucugcc cuggaguaug g guauggugc   1560
agcuggcuau gauggagacu ucaaucucga cagcgaugaa uggacuguug g uucuucauc   1620
cuccgucucc ucaggcuccu ugaguccccgu ugacgaucau uacucauggg a aaccgaggc   1680
acugaccucc ccacauacug auauugaguc cggcaggcau acuuucagcc c uugaguagc   1740
cacaaaccaa acucgauacc ugcauauagc gaucucgcuc cuccuccacu g caucuauuu   1800
acgagacggc guuagaacau uucacgacau ucuggcuuua uugcaucgag c acauuucga   1860
cacauauauc uuuaauaccc uuucuucggu gucccagauc aucgguucga c cuuaaugua   1920
ccucgguccg aauccgccug ggauacuguu ucucuuuccg ccgcacuuca c uguacauug   1980
cuugacauug cgaaaccggg uugggcucga acgugggaug gguuaucgcu c aucgcuaca   2040
cgccguugcu ccaucauaau guuaauggac acaaugggc uacgcauccu g guguuuagu   2100
ccuggaagac cauccgauaa cccccgucgg uaacacucgc uugucucgug u ccacccaga   2160
cacuacuuca auucucacuu cuaucguccg cuauuaccuu gaccuggucg a acccauccu   2220
uauuauucgu uucgacuaug cuauauauuu auuuuuacca uucgugucga u cgcucauac   2280
ucuuggcgcu ugggacugga agcauuuaua uuggaaaaaa ucacggaaug g ggcgccuuu   2340
ucuucuugca cuucacucgc ugugcauaga cgguuuuaca uuucugcuuu g caaugcauc   2400
acgaacucug cauuagcaua uagaaagagg ggaaggaugg accuucuucu u gauugcucg   2460
caugguuuau ccauucgcuc aaaguggauu acguccacau cuuacccggg g gcuauacac   2520
auggcuacug uguugcuuuc ugacauucgc cggacgugca agguugggag g agagucuga   2580
cgcugacggg gcuuguugaa ggauguucac gcgucccgau uugacccggc u ucgacuaac   2640
cucagauucu cgacuuguug gacggugacu ugacuugcuu gcuauggucu g acgcucuca   2700
caccuaccua ucacauccuc cucaccucac aaauuccgcu cauggacacu a uccucuucu   2760
uuucguuucc cuuggauagu gugugugugu gugugguugg ggcaaauuau c cauagcagc   2820
aguauuauua guuauaaucc gguaguguua ugauuuauga aggcaacuug u auacua      2877
```

<210> SEQ ID NO 19
<211> LENGTH: 3220

-continued

<212> TYPE: DNA
<213> ORGANISM: Candida neoformans
<220> FEATURE:
<221> NAME/KEY: intron
<222> LOCATION: (1888)..(1939)

<400> SEQUENCE: 19 gtcgacatag ttacactccc ctctactctt cagactaccc cttctgatta t caggagact 60 acgactactc cgcctacctt gacctttgca aactcggagc cacgaccgag t ccttccctc 120 catcgttccc tgcgcaacat cggtttggcc gacggcagca tgacttgtgc c ccaggctat 180 atcctcatct gcattcatca tgacccttg tctcgttaca cgcttggcat c aattttacc 240 acctttgtgg gtctttgccc cacgacccct gctagtacca gcacttccgg c ggtcccgcc 300 ttttcctctt ttacacccaa gttcgccgac catatgcgat gtcatgtcat c cagcgcttg 360 ctgcacactg tcatgcacga ccgtctcgcc aacatgccgg gttgccacac c tgggaatcg 420 ttggtcaatg cggcgtaccg ttactgcacc tgggctatgg aatgtatctt c ctcggcacc 480 gatgcaaatg ttcaattcgg gattgcttgt tatccccact tgaaagagct c gaagaggcg 540 gcaaggacgc tcaggaagga tagtatgggc gagtgggatg atgtggtgca g attggggtg 600 gataggttgt tggaaatact accttgtggt gaacggacct tgatcaacaa g agaaggatc 660 gaaaaggaac gactgcaagc gcttctaaaa gctcaaactc aagtcaaggc c aagcatgag 720 gccagatgtc aggtggcaac cccgatccca gctccagctg tcattcctgt c tctgcacct 780 gctccggtta taatcaagcg taaaaaatac agtagcctac gcaagctgat g ggacgtgcg 840 gggtcggtga ttggcaggca gaagatgcgg gcaagggcgt ctgcgattat c gagaaggga 900 aaggccggct tctacgatag gcaaaaggtc cagcgcatgg agccggctcc a tccatgtct 960 cgtcctgcgg gagtgtcttg tgtgtgattg tcagctggcc gtgaagatag t cttggagct 1020 gtgtataggg atactacatg atgtgcatgc agtgtgtttt caaagcaatt g ccacgtggt 1080 gttcgcgtgg gtcggaaacg aggttcgcgt tgttatggtt cttgttttga g attctcgcg 1140 ctggctacac gtacgcacca tacactgcag acgacagcgg caagcataca g acggcaacg 1200 ctgacatccc agccacacac accatgtccg ccatccgcgc actcacgagc c ccgtcaccg 1260 cctgcttctc cacctctctc tccccgcatg ccgcattcca ccgcttcctc c atgcgctct 1320 ccgcctccat ccgccgcctc gacctctccc gcgacccgcg caagaccttg g accgcctca 1380 ggcagcacag gttcaccctt gccaacactt tgccccgcgc gttcatgctt c tgtgcgcct 1440 cctacagtct ctacatcatg accaccccgc ccttcccact caagctcggg a tacccatcg 1500 catacatcgc cgctgtcatc ttcccgatca cgtcgcagtt tgtctggccg g cgacaccca 1560 tctttgcatg gctcatcacc tttttctccg cccgtttcat cccttccggc c gccggcccg 1620 aaatccacgt cgcccttctc ccagcccttg aatccgtcct ctacggtgcc a acatttctg 1680 atctccaaac acgatatacc aacgctttcc ttgatgtggt cgcctggctg c cctatgggg 1740 tattacattt cacccttcca ttcgtcgtgg ctgttatcct ttggtcactg g gacctaggg 1800 gtgcggttca gttctggggt ttggcctttg ggtggatgaa tttgctcggt g tcgtctgcc 1860 agctcctctt ccctgctgcc gcgccttgta agtacctctc tcttttattt a atatatcca 1920 tacttaatat gccgggcagg gtacgaaatc attcacggtc ttacccccgc c gactattcc 1980 atggctggct ctcccggcgg tctcatgcgt atcgaccgcg tcttccattc t tcaggctat 2040 accaacgcat tcggttccgc tcctcttgtt tttggcgcct tcccctccct c cattcagga 2100 tgtgccgtca tggaagccct cttcctctcc catttcttcc catccctcaa g ggcctgtat 2160

-continued

```
tggggctatg tcggtgtcct ctggtgggcg accatgtacc tctcccacca c tacctcatc   2220

gacctcgttg gcggagcttg tctgagcgtc ttggtgttct acttgtgcat g cctgaaggt   2280

ttcaaggacg ttgatcagat acagtgggag gcggtggaag gggatggata c gagatgatt   2340

ggcggaccca gaacaggcac aggtcctgag attgatttgg atgaggaaat t agaaagttg   2400

gaagaacaag gcgaagcgct ttttgagcag gtgatagggg atgaagagtc t cggatcgag   2460

acaaggggag aaggaaacag tggcgcgggc gggaatctga gtgggaatga a agtggtgat   2520

agtgcagata gcggtagggg aaagggcaag gggaagggga aggggaaaca a actgccaaa   2580

aagccaaagg cgaaggagca aagatcggtt agctggggag aaacaaaggt g atgggtgaa   2640

ggagcgcagg tggcttcaga gaatagctct tagatatctg ttttaaaaca g tagtatacc   2700

caacaatttt ttgacgatat accctaccac tatgatctta ataatgcaga a tagaaaaac   2760

accttgcccc tctcgcaggc gtcaacacat ggagtctagg cagttaaatc a cactacatc   2820

atcatcgccg aaaaaaataa acctagtaac tccaacccaa ccctcctggt a caggcctgt   2880

tcgtccaccg actgataatt cccatcgccc tcgccctcct cacaagttta c ccacccgcc   2940

tttgcgactt ccaagtcaac ccggtctccg cccgacttct tatcttgccc a tcgggttga   3000

cgaattcata ggcgaaatta gggttcatat cgtgcaccaa ggggttcgtt t tggtgatgt   3060

aaaaaggatc aagcttgacg gcgattttct tgggaggacc aagaagaggt g gacggggca   3120

aaggtcgagc ggtggggtag atggattctt gggtgaatgc ttgaggggca g taaactaga   3180

agagttgaga aaacccaaag gagtcagcct ttatgtcgac                         3220
```

<210> SEQ ID NO 20
<211> LENGTH: 3120
<212> TYPE: DNA
<213> ORGANISM: Cryptococcus neoformans
<220> FEATURE:
<221> NAME/KEY: CDS
<222> LOCATION: (1224)..(2624)

<400> SEQUENCE: 20

```
gtcgacatag ttacactccc ctctactctt cagactaccc cttctgatta t caggagact     60

acgactactc cgcctacctt gacctttgca aactcggagc cacgaccgag t ccttccctc    120

catcgttccc tgcgcaacat cggtttggcc gacggcagca tgacttgtgc c ccaggctat    180

atcctcatct gcattcatca tgaccccttg tctcgttaca cgcttggcat c aattttacc    240

acctttgtgg gtctttgccc cacgacccct gctagtacca gcacttccgg c ggtcccgcc    300

ttttcctctt ttacacccaa gttcgccgac catatgcgat gtcatgtcat c cagcgcttg    360

ctgcacactg tcatgcacga ccgtctcgcc aacatgccgg gttgccacac c tgggaatcg    420

ttggtcaatg cggcgtaccg ttactgcacc tgggctatgg aatgtatctt c ctcggcacc    480

gatgcaaatg ttcaattcgg gattgcttgt tatccccact tgaaagagct c gaagaggcg    540

gcaaggacgc tcaggaagga tagtatgggc gagtgggatg atgtggtgca g attggggtg    600

gataggttgt tggaaatact accttgtggt gaacggacct tgatcaacaa g agaaggatc    660

gaaaaggaac gactgcaagc gcttctaaaa gctcaaactc aagtcaaggc c aagcatgag    720

gccagatgtc aggtggcaac cccgatccca gctccagctg tcattcctgt c tctgcacct    780

gctccggtta taatcaagcg taaaaaatac agtagcctac gcaagctgat g ggacgtgcg    840

gggtcggtga ttggcaggca gaagatgcgg gcaagggcgt ctgcgattat c gagaaggga    900

aaggccggct tctacgatag gcaaaaggtc cagcgcatgg agccggctcc a tccatgtct    960
```

-continued

```
cgtcctgcgg gagtgtcttg tgtgtgattg tcagctggcc gtgaagatag t cttggagct   1020

gtgtataggg atactacatg atgtgcatgc agtgtgtttt caaagcaatt g ccacgtggt   1080

gttcgcgtgg gtcggaaacg aggttcgcgt tgttatggtt cttgttttga g attctcgcg   1140

ctggctacac gtacgcacca tacactgcag acgacagcgg caagcataca g acggcaacg   1200

ctgacatccc agccacacac acc atg tcc gcc atc cgc g ca ctc acg agc ccc   1253
                          Met Ser Ala Ile Arg Ala Leu Thr Ser Pro
                            1               5                  10

gtc acc gcc tgc ttc tcc acc tct ctc tcc c cg cat gcc gca ttc cac     1301
Val Thr Ala Cys Phe Ser Thr Ser Leu Ser P ro His Ala Ala Phe His
                15                  20                  25

cgc ttc ctc cat gcg ctc tcc gcc tcc atc c gc cgc ctc gac ctc tcc     1349
Arg Phe Leu His Ala Leu Ser Ala Ser Ile A rg Arg Leu Asp Leu Ser
            30                  35                  40

cgc gac ccg cgc aag acc ttg gac cgc ctc a gg cag cac agg ttc acc     1397
Arg Asp Pro Arg Lys Thr Leu Asp Arg Leu A rg Gln His Arg Phe Thr
        45                  50                  55

ctt gcc aac act ttg ccc cgc gcg ttc atg c tt ctg tgc gcc tcc tac     1445
Leu Ala Asn Thr Leu Pro Arg Ala Phe Met L eu Leu Cys Ala Ser Tyr
    60                  65                  70

agt ctc tac atc atg acc acc ccg ccc ttc c ca ctc aag ctc ggg ata     1493
Ser Leu Tyr Ile Met Thr Thr Pro Pro Phe P ro Leu Lys Leu Gly Ile
75                  80                  85                  90

ccc atc gca tac atc gcc gct gtc atc ttc c cg atc acg tcg cag tcc     1541
Pro Ile Ala Tyr Ile Ala Ala Val Ile Phe P ro Ile Thr Ser Gln Ser
                95                  100                 105

gcc cgt ttc atc cct tcc ggc cgc cgg ccc g aa atc cac gtc gcc ctt     1589
Ala Arg Phe Ile Pro Ser Gly Arg Arg Pro G lu Ile His Val Ala Leu
            110                 115                 120

ctc cca gcc ctt gaa tcc gtc ctc tac ggt g cc aac att tct gat ctc     1637
Leu Pro Ala Leu Glu Ser Val Leu Tyr Gly A la Asn Ile Ser Asp Leu
        125                 130                 135

caa aca cga tat acc aac gct ttc ctt gat g tg gtc gcc tgg ctg ccc     1685
Gln Thr Arg Tyr Thr Asn Ala Phe Leu Asp V al Val Ala Trp Leu Pro
    140                 145                 150

tat ggg gta tta cat ttc acc ctt cca ttc g tc gtg gct gtt atc ctt     1733
Tyr Gly Val Leu His Phe Thr Leu Pro Phe V al Val Ala Val Ile Leu
155                 160                 165                 170

tgg tca ctg gga cct agg ggt gcg gtt cag t tc tgg ggt ttg gcc ttt     1781
Trp Ser Leu Gly Pro Arg Gly Ala Val Gln P he Trp Gly Leu Ala Phe
                175                 180                 185

ggg tgg atg aat ttg ctc ggt gtc gtc tgc c ag ctc ctc ttc cct gct     1829
Gly Trp Met Asn Leu Leu Gly Val Val Cys G ln Leu Leu Phe Pro Ala
            190                 195                 200

gcc gcg cct tgg tac gaa atc att cac ggt c tt acc ccc gcc gac tat     1877
Ala Ala Pro Trp Tyr Glu Ile Ile His Gly L eu Thr Pro Ala Asp Tyr
        205                 210                 215

tcc atg gct ggc tct ccc ggc ggt ctc atg c gt atc gac cgc gtc ttc     1925
Ser Met Ala Gly Ser Pro Gly Gly Leu Met A rg Ile Asp Arg Val Phe
    220                 225                 230

cat tct tca ggc tat acc aac gca ttc ggt t cc gct cct ctt gtt ttt     1973
His Ser Ser Gly Tyr Thr Asn Ala Phe Gly S er Ala Pro Leu Val Phe
235                 240                 245                 250

ggc gcc ttc ccc tcc ctc cat tca gga tgt g cc gtc atg gaa gcc ctc     2021
Gly Ala Phe Pro Ser Leu His Ser Gly Cys A la Val Met Glu Ala Leu
                255                 260                 265

ttc ctc tcc cat ttc ttc cca tcc ctc aag g gc ctg tat tgg ggc tat     2069
Phe Leu Ser His Phe Phe Pro Ser Leu Lys G ly Leu Tyr Trp Gly Tyr
```

-continued

```
            270                 275                 280

gtc ggt gtc ctc tgg tgg gcg acc atg tac c tc tcc cac cac tac ctc     2117
Val Gly Val Leu Trp Trp Ala Thr Met Tyr L eu Ser His His Tyr Leu
        285                 290                 295

atc gac ctc gtt ggc gga gct tgt ctg agc g tc ttg gtg ttc tac ttg     2165
Ile Asp Leu Val Gly Gly Ala Cys Leu Ser V al Leu Val Phe Tyr Leu
    300                 305                 310

tgc atg cct gaa ggt ttc aag gac gtt gat c ag ata cag tgg gag gcg     2213
Cys Met Pro Glu Gly Phe Lys Asp Val Asp G ln Ile Gln Trp Glu Ala
315                 320                 325                 330

gtg gaa ggg gat gga tac gag atg att ggc g ga ccc aga aca ggc aca     2261
Val Glu Gly Asp Gly Tyr Glu Met Ile Gly G ly Pro Arg Thr Gly Thr
                335                 340                 345

ggt cct gag att gat ttg gat gag gaa att a ga aag ttg gaa gaa caa     2309
Gly Pro Glu Ile Asp Leu Asp Glu Glu Ile A rg Lys Leu Glu Glu Gln
            350                 355                 360

ggc gaa gcg ctt ttt gag cag gtg ata ggg g at gaa gag tct cgg atc     2357
Gly Glu Ala Leu Phe Glu Gln Val Ile Gly A sp Glu Glu Ser Arg Ile
        365                 370                 375

gag aca agg gga gaa gga aac agt ggc gcg g gc ggg aat ctg agt ggg     2405
Glu Thr Arg Gly Glu Gly Asn Ser Gly Ala G ly Gly Asn Leu Ser Gly
    380                 385                 390

aat gaa agt ggt gat agt gca gat agc ggt a gg gga aag ggc aag ggg     2453
Asn Glu Ser Gly Asp Ser Ala Asp Ser Gly A rg Gly Lys Gly Lys Gly
395                 400                 405                 410

aag ggg aag ggg aaa caa act gcc aaa aag c ca aag gcg aag gag caa     2501
Lys Gly Lys Gly Lys Gln Thr Ala Lys Lys P ro Lys Ala Lys Glu Gln
                415                 420                 425

aga tcg gtt agc tgg gga gaa aca aag gtg a tg ggt gaa gga gcg cag     2549
Arg Ser Val Ser Trp Gly Glu Thr Lys Val M et Gly Glu Gly Ala Gln
            430                 435                 440

gtg gct tca gag aat agc tct tag ata tct g tt tta aaa cag tag tat     2597
Val Ala Ser Glu Asn Ser Ser     Ile Ser Val Leu Lys Gln     Tyr
        445                 450                 455

acc caa caa ttt ttt gac gat ata ccc taccacta tg atcttaataa           2644
Thr Gln Gln Phe Phe Asp Asp Ile Pro
    460                 465

tgcagaatag aaaaacacct tgcccctctc gcaggcgtca acacatggag t ctaggcagt   2704

taaatcacac tacatcatca tcgccgaaaa aaataaacct agtaactcca a cccaaccct   2764

cctggtacag gcctgttcgt ccaccgactg ataattccca tcgccctcgc c ctcctcaca   2824

agtttaccca cccgcctttg cgacttccaa gtcaacccgg tctccgcccg a cttcttatc   2884

ttgcccatcg ggttgacgaa ttcataggcg aaattagggt tcatatcgtg c accaagggg   2944

ttcgttttgg tgatgtaaaa aggatcaagc ttgacggcga ttttcttggg a ggaccaaga   3004

agaggtggac ggggcaaagg tcgagcggtg gggtagatgg attcttgggt g aatgcttga   3064

ggggcagtaa actagaagag ttgagaaaac ccaaaggagt cagcctttat g tcgac       3120


<210> SEQ ID NO 21
<211> LENGTH: 449
<212> TYPE: PRT
<213> ORGANISM: Cryptococcus neoformans

<400> SEQUENCE: 21

Met Ser Ala Ile Arg Ala Leu Thr Ser Pro V al Thr Ala Cys Phe Ser
  1               5                  10                  15

Thr Ser Leu Ser Pro His Ala Ala Phe His A rg Phe Leu His Ala Leu
            20                  25                  30
```

-continued

```
Ser Ala Ser Ile Arg Arg Leu Asp Leu Ser A rg Asp Pro Arg Lys Thr
         35                  40                  45

Leu Asp Arg Leu Arg Gln His Arg Phe Thr L eu Ala Asn Thr Leu Pro
     50                  55                  60

Arg Ala Phe Met Leu Leu Cys Ala Ser Tyr S er Leu Tyr Ile Met Thr
 65                  70                  75                  80

Thr Pro Pro Phe Pro Leu Lys Leu Gly Ile P ro Ile Ala Tyr Ile Ala
                 85                  90                  95

Ala Val Ile Phe Pro Ile Thr Ser Gln Ser A la Arg Phe Ile Pro Ser
            100                 105                 110

Gly Arg Arg Pro Glu Ile His Val Ala Leu L eu Pro Ala Leu Glu Ser
        115                 120                 125

Val Leu Tyr Gly Ala Asn Ile Ser Asp Leu G ln Thr Arg Tyr Thr Asn
    130                 135                 140

Ala Phe Leu Asp Val Val Ala Trp Leu Pro T yr Gly Val Leu His Phe
145                 150                 155                 160

Thr Leu Pro Phe Val Val Ala Val Ile Leu T rp Ser Leu Gly Pro Arg
                165                 170                 175

Gly Ala Val Gln Phe Trp Gly Leu Ala Phe G ly Trp Met Asn Leu Leu
            180                 185                 190

Gly Val Val Cys Gln Leu Leu Phe Pro Ala A la Ala Pro Trp Tyr Glu
        195                 200                 205

Ile Ile His Gly Leu Thr Pro Ala Asp Tyr S er Met Ala Gly Ser Pro
    210                 215                 220

Gly Gly Leu Met Arg Ile Asp Arg Val Phe H is Ser Ser Gly Tyr Thr
225                 230                 235                 240

Asn Ala Phe Gly Ser Ala Pro Leu Val Phe G ly Ala Phe Pro Ser Leu
                245                 250                 255

His Ser Gly Cys Ala Val Met Glu Ala Leu P he Leu Ser His Phe Phe
            260                 265                 270

Pro Ser Leu Lys Gly Leu Tyr Trp Gly Tyr V al Gly Val Leu Trp Trp
        275                 280                 285

Ala Thr Met Tyr Leu Ser His His Tyr Leu I le Asp Leu Val Gly Gly
    290                 295                 300

Ala Cys Leu Ser Val Leu Val Phe Tyr Leu C ys Met Pro Glu Gly Phe
305                 310                 315                 320

Lys Asp Val Asp Gln Ile Gln Trp Glu Ala V al Glu Gly Asp Gly Tyr
                325                 330                 335

Glu Met Ile Gly Gly Pro Arg Thr Gly Thr G ly Pro Glu Ile Asp Leu
            340                 345                 350

Asp Glu Glu Ile Arg Lys Leu Glu Glu Gln G ly Glu Ala Leu Phe Glu
        355                 360                 365

Gln Val Ile Gly Asp Glu Glu Ser Arg Ile G lu Thr Arg Gly Glu Gly
    370                 375                 380

Asn Ser Gly Ala Gly Gly Asn Leu Ser Gly A sn Glu Ser Gly Asp Ser
385                 390                 395                 400

Ala Asp Ser Gly Arg Gly Lys Gly Lys Gly L ys Gly Lys Gly Lys Gln
                405                 410                 415

Thr Ala Lys Lys Pro Lys Ala Lys Glu Gln A rg Ser Val Ser Trp Gly
            420                 425                 430

Glu Thr Lys Val Met Gly Glu Gly Ala Gln V al Ala Ser Glu Asn Ser
        435                 440                 445
```

-continued

Ser

<210> SEQ ID NO 22
<211> LENGTH: 6
<212> TYPE: PRT
<213> ORGANISM: Cryptococcus neoformans

<400> SEQUENCE: 22

Ile Ser Val Leu Lys Gln
1 5

<210> SEQ ID NO 23
<211> LENGTH: 10
<212> TYPE: PRT
<213> ORGANISM: Cryptococcus neoformans

<400> SEQUENCE: 23

Tyr Thr Gln Gln Phe Phe Asp Asp Ile Pro
1 5 10

<210> SEQ ID NO 24
<211> LENGTH: 3168
<212> TYPE: RNA
<213> ORGANISM: Candida neoformans

<400> SEQUENCE: 24 gucgacauag uuacacuccc cucuacucuu cagacuaccc cuucugauua u caggagacu 60 acgacuacuc cgccuaccuu gaccuuugca aacucggagc cacgaccgag u ccuucccuc 120 caucguuccc ugcgcaacau cgguuuggcc gacggcagca ugacuugugc c ccaggcuau 180 auccucaucu gcauucauca ugaccccuug ucucguuaca cgcuuggcau c aauuuuacc 240 accuuugugg gucuuugccc cacgaccccu gcuaguacca gcacuuccgg c ggucccgcc 300 uuuuccucuu uuacacccaa guucgccgac cauaugcgau gucaugucau c cagcgcuug 360 cugcacacug ucaugcacga ccgucucgcc aacaugccgg guugccacac c ugggaaucg 420 uuggucaaug cggcguaccg uuacugcacc ugggcuaugg aauguaucuu c cucggcacc 480 gaugcaaaug uucaauucgg gauugcuugu uaucccccacu ugaaagagcu c gaagaggcg 540 gcaaggacgc ucaggaagga uaguaugggc gaguggggaug auguggugca g auuggggug 600 gauagguugu uggaaauacu accuuguggu gaacggaccu ugaucaacaa g agaaggauc 660 gaaaaggaac gacugcaagc gcuucuaaaa gcucaaacuc aagucaaggc c aagcaugag 720 gccagauguc agguggcaac cccgauccca gcuccagcug ucauuccugu c ucugcaccu 780 gcuccgguua uaaucaagcg uaaaaaauac aguagccuac gcaagcugau g ggacgugcg 840 gggucgguga uuggcaggca gaagaugcgg gcaagggcgu cugcgauuau c gagaaggga 900 aaggccggcu ucuacgauag gcaaaagguc cagcgcaugg agccggcucc a uccaugucu 960 cguccugcgg gagugucuug ugugugauug ucagcuggcc gugaagauag u cuuggagcu 1020 guguauaggg auacuacaug augugcaugc agugugguuu caaagcaauu g ccacguggu 1080 guucgcgugg gucggaaacg agguucgcgu uguuaugguu cuuguuuuga g auucucgcg 1140 cuggcuacac guacgcacca uacacugcag acgacagcgg caagcauaca g acggcaacg 1200 cugacauccc agccacacac accauguccg ccauccgcgc acucacgagc c ccgucaccg 1260 ccugcuucuc caccucucuc uccccgcaug ccgcauucca ccgcuuccuc c augcgcucu 1320 ccgccuccau ccgccgccuc gaccucuccc gcgacccgcg caagaccuug g accgccuca 1380 ggcagcacag guucacccuu gccaacacuu ugccccgcgc guucaugcuu c ugugcgccu 1440

-continued

```
ccuacagucu cuacaucaug accaccccgc ccuucccacu caagcucggg a uacccaucg   1500
cauacaucgc cgcugucauc uucccgauca cgucgcaguu ugucuggccg g cgacaccca   1560
ucuuugcaug gcucaucacc uuuuucuccg cccguuucau cccuuccggc c gccggcccg   1620
aaauccacgu cgcccuucuc ccagcccuug aauccguccu cuacggugcc a acauuucug   1680
aucuccaaac acgauauacc aacgcuuucc uugauguggu cgccuggcug c ccuaugggg   1740
uauuacauuu cacccuucca uucgucgugg cuguuauccu uuggucacug g gaccuaggg   1800
gugcgguuca guucuggggu uuggccuuug gguggaugaa uuugcucggu g ucgucugcc   1860
agcuccucuu cccugcugcc gcgccuuggu acgaaaucau ucacggucuu a cccccgccg   1920
acuauuccau ggcuggcucu cccggcgguc ucaugcguau cgaccgcguc u uccauucuu   1980
caggcuauac caacgcauuc gguuccgcuc cucuuguuuu uggcgccuuc c ccucccucc   2040
auucaggaug ugccgucaug gaagcccucu uccucuccca uuucuuccca u cccucaagg   2100
gccuguauug gggcuauguc gguguccucu gguggggcgac cauguaccuc u cccaccacu   2160
accucaucga ccucguuggc ggagcuuguc ugagcgucuu gguguucuac u ugugcaugc   2220
cugaagguuu caaggacguu gaucagauac aguggggaggc gguggaaggg g auggauacg   2280
agaugauugg cggacccaga acaggcacag guccugagau ugauuuggau g aggaaauua   2340
gaaaguugga agaacaaggc gaagcgcuuu uugagcaggu gauaggggau g aagagucuc   2400
ggaucgagac aaggggagaa ggaaacagug gcgcgggcgg gaaucugagu g ggaaugaaa   2460
guggugauag ugcagauagc gguaggggaa agggcaaggg gaaggggaag g ggaaacaaa   2520
cugccaaaaa gccaaaggcg aaggagcaaa gaucgguuag cuggggagaa a caaagguga   2580
ugggugaagg agcgcaggug gcuucagaga auagcucuua gauaucuguu u uaaaacagu   2640
aguauaccca acaauuuuuu gacgauauac ccuaccacua ugaucuuaau a augcagaau   2700
agaaaaacac cuugccccuc ucgcaggcgu caacacaugg agucuaggca g uuaaaucac   2760
acuacaucau caucgccgaa aaaaauaaac cuaguaacuc caacccaacc c uccugguac   2820
aggccuguuc guccaccgac ugauaauucc caucgcccuc gcccuccuca c aaguuuacc   2880
cacccgccuu ugcgacuucc aagucaaccc ggucuccgcc cgacuucuua u cuugcccau   2940
cggguugacg aauucauagg cgaaauuagg guucauaucg ugcaccaagg g guucguuuu   3000
ggugauguaa aaaggaucaa gcuugacggc gauuuucuug ggaggaccaa g aagaggugg   3060
acggggcaaa ggucgagcgg ugggguagau ggauucuugg gugaaugcuu g aggggcagu   3120
aaacuagaag aguugagaaa acccaaagga gucagccuuu augucgac                3168
```

We claim:

1. An isolated inositolphoshoryl ceramide (IPC) synthase protein from a fungal cell comprising the amino acid sequence shown in SEQ ID NO:2.

2. An isolated inositolphosphoryl ceramide (IPC) synthase protein from a fungal cell consisting of the amino acid sequence shown in SEQ ID NO:2.

* * * * *